US011266654B2

(12) United States Patent
Lichenstein et al.

(10) Patent No.: US 11,266,654 B2
(45) Date of Patent: *Mar. 8, 2022

(54) APILIMOD COMPOSITIONS AND METHODS FOR USING SAME

(71) Applicant: AI Therapeutics, Inc., Guilford, CT (US)

(72) Inventors: Henri Lichenstein, Guilford, CT (US); Jonathan M. Rothberg, Guilford, CT (US); Sophia Gayle, East Haven, CT (US); Neil Beeharry, Guilford, CT (US); Paul Beckett, Yorktown Heights, NY (US); Sean Landrette, Meriden, CT (US); Chris Conrad, Guilford, CT (US); Matt Dyer, Heber City, UT (US); Tian Xu, Shanghai (CN)

(73) Assignee: AI Therapeutics, Inc., Guilford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/728,566

(22) Filed: Dec. 27, 2019

(65) Prior Publication Data

US 2020/0268764 A1    Aug. 27, 2020

Related U.S. Application Data

(63) Continuation of application No. 16/193,045, filed on Nov. 16, 2018, now abandoned, which is a continuation of application No. 15/113,154, filed as application No. PCT/US2015/012733 on Jan. 23, 2015, now Pat. No. 10,179,135.

(60) Provisional application No. 62/077,127, filed on Nov. 7, 2014, provisional application No. 61/931,078, filed on Jan. 24, 2014, provisional application No. 61/931,075, filed on Jan. 24, 2014.

(51) Int. Cl.

| A61K 31/5377 | (2006.01) |
| A61K 31/44 | (2006.01) |
| A61K 31/506 | (2006.01) |
| A61K 31/404 | (2006.01) |
| A61K 31/4178 | (2006.01) |
| A61K 31/475 | (2006.01) |
| A61K 31/573 | (2006.01) |
| A61K 31/704 | (2006.01) |
| A61K 45/06 | (2006.01) |
| A61K 9/00 | (2006.01) |
| A61K 31/436 | (2006.01) |
| A61K 31/519 | (2006.01) |
| A61K 31/675 | (2006.01) |
| A61K 31/69 | (2006.01) |

(52) U.S. Cl.
CPC ........ *A61K 31/5377* (2013.01); *A61K 9/0019* (2013.01); *A61K 31/404* (2013.01); *A61K 31/4178* (2013.01); *A61K 31/436* (2013.01); *A61K 31/44* (2013.01); *A61K 31/475* (2013.01); *A61K 31/506* (2013.01); *A61K 31/519* (2013.01); *A61K 31/573* (2013.01); *A61K 31/675* (2013.01); *A61K 31/69* (2013.01); *A61K 31/704* (2013.01); *A61K 45/06* (2013.01)

(58) Field of Classification Search
CPC ... A61K 31/5377; A61K 31/44; A61K 31/506
See application file for complete search history.

(56) References Cited

U.S. PATENT DOCUMENTS

| 5,210,015 A | 5/1993 | Gelfand et al. |
| 5,487,972 A | 1/1996 | Gelfand et al. |
| 6,660,733 B2 | 12/2003 | Sun et al. |
| 6,693,097 B2 | 2/2004 | Ono et al. |
| 6,858,606 B2 | 2/2005 | Sun et al. |
| 7,745,436 B2 | 6/2010 | Kostik et al. |
| 7,863,270 B2 | 1/2011 | Demko et al. |
| 7,923,557 B2 | 4/2011 | Zhang et al. |
| 9,295,731 B2 | 3/2016 | Nguyen |
| 10,179,135 B2 | 1/2019 | Lichenstein et al. |
| 10,206,910 B2 | 2/2019 | Beeharry et al. |
| 10,350,213 B2 | 7/2019 | Lichenstein et al. |
| 10,765,682 B2 | 9/2020 | Beeharry et al. |
| 2007/0112005 A1 | 5/2007 | Chen et al. |
| 2007/0149521 A1 | 6/2007 | Crew et al. |
| 2007/0254883 A1 | 11/2007 | Crew et al. |
| 2009/0312319 A1 | 12/2009 | Ren et al. |
| 2010/0015140 A1 | 1/2010 | Danter |
| 2010/0048547 A1 | 2/2010 | Atallah et al. |
| 2011/0081338 A1 | 4/2011 | Roberts et al. |
| 2011/0277018 A1 | 11/2011 | Weizman |
| 2011/0287018 A1 | 11/2011 | Bosch |
| 2013/0267521 A1 | 10/2013 | Castro et al. |
| 2014/0105891 A1 | 4/2014 | Garmey et al. |

(Continued)

FOREIGN PATENT DOCUMENTS

| CN | 102905707 A | 1/2013 |
| CN | 106659716 A | 5/2017 |

(Continued)

OTHER PUBLICATIONS

Official Office action (English translation) dated Feb. 5, 2019 for Japanese Patent Application No. 2016-548172, filed Jan. 23, 2015. References listed on p. 3. 3 pages.
Chinese Search Report issued in Chinese Application No. 201580072613.9, dated Dec. 26, 2019, (2 pages of English Translation & 2 pages of Foreign Language).
Chinese Search Report received for Chinese Patent Application No. 201580072608.8, dated Oct. 8, 2019, 4 pages (Foreign language).
Chinese Search Report received for Chinese Patent Application No. 201580072610.5, dated Nov. 4, 2019, 3 pages.

(Continued)

*Primary Examiner* — Samira J Jean-Louis
(74) *Attorney, Agent, or Firm* — Muriel Liberto; Mintz Levin Cohn Ferris Glovsky and Popeo, P.C.

(57) ABSTRACT

The present invention relates to methods for treating cancer with apilimod and related compositions and methods.

9 Claims, 21 Drawing Sheets

(56) References Cited

U.S. PATENT DOCUMENTS

| | | |
|---|---|---|
| 2017/0007613 A1 | 1/2017 | Lichenstein et al. |
| 2017/0020884 A1 | 1/2017 | Lichenstein et al. |
| 2017/0333408 A1 | 11/2017 | Beeharry et al. |
| 2017/0333439 A1 | 11/2017 | Beeharry et al. |
| 2018/0015098 A1 | 1/2018 | Lichenstein et al. |
| 2018/0078561 A1 | 3/2018 | Beckett et al. |
| 2019/0183902 A1 | 6/2019 | Lichenstein et al. |
| 2019/0201385 A1 | 7/2019 | Beeharry et al. |
| 2019/0209576 A1 | 7/2019 | Beeharry et al. |
| 2020/0297706 A1 | 9/2020 | Beeharry et al. |
| 2021/0077500 A1 | 3/2021 | Landrette et al. |

FOREIGN PATENT DOCUMENTS

| | | |
|---|---|---|
| EA | 009873 B1 | 4/2008 |
| JP | 2007532667 A | 11/2007 |
| JP | 2009209069 A | 9/2009 |
| JP | 2013522212 A | 6/2013 |
| JP | 2013542980 A | 11/2013 |
| MX | 2016009590 A | 5/2017 |
| RU | 2438664 C2 | 1/2012 |
| RU | 2486183 C9 | 1/2014 |
| RU | 2013110124 A | 9/2014 |
| WO | 95/13399 A1 | 5/1995 |
| WO | 2005076843 A2 | 8/2005 |
| WO | 2005112938 A2 | 12/2005 |
| WO | 2005076843 A3 | 1/2006 |
| WO | 2006029385 A2 | 3/2006 |
| WO | 2006128129 A2 | 11/2006 |
| WO | 2008008433 A2 | 1/2008 |
| WO | 2008008433 A3 | 9/2008 |
| WO | 2006128129 A3 | 10/2008 |
| WO | 2010/006072 A2 | 1/2010 |
| WO | 2011112635 A1 | 9/2011 |
| WO | 2011146727 A1 | 11/2011 |
| WO | 2012066518 A1 | 5/2012 |
| WO | 2013152342 A1 | 10/2013 |
| WO | 2013/173223 A1 | 11/2013 |
| WO | 2015112888 A1 | 7/2015 |
| WO | 2016/073871 A1 | 5/2016 |
| WO | 2016/073877 A1 | 5/2016 |
| WO | 2016/073884 A1 | 5/2016 |
| WO | 2020009971 A1 | 1/2020 |
| WO | 2021051135 A1 | 3/2021 |

OTHER PUBLICATIONS (2018) Definition of stage III melanoma—NCI Dictionary of Cancer Terms—National Cancer Institute, Available at: https://www.cancer.gov/publications/dictionaries/cancer-terms/def/stage-iii-melanoma, 2 pages.
(2018) Definition of stage IV melanoma—NCI Dictionary of Cancer Terms—National Cancer Institute, (https://www.cancer.gov/publications/dictionaries/cancer-terms/def/stage-iv-melanoma) 1 page.
Extended European Search Report issued in European Application No. 19171060.7, dated Nov. 15, 2019, 4 pages.
International Preliminary Report on Patentability in International Application No. PCT/US2015/012733, dated Jul. 26, 2016, 6 pages.
International Preliminary Report on Patentability received for PCT Application No. PCT/US2015/059512, dated May 9, 2017, 06 pages.
International Preliminary Report on Patentability received for PCT Application No. PCT/US2015/059526, dated May 9, 2017, 08 pages.
International Search Report and Written Opinion received for PCT Application No. PCT/US2015/059512, dated Dec. 23, 2015, 09 pages.
International Search Report for International Application No. PCT/US2015/059502, filed Nov. 6, 2015, dated Dec. 23, 2015, 04 pages.
International Search Report received for PCT Application No. PCT/US2015/059526, dated Dec. 23, 2015, 11 pages.
International Search Report received for PCT Application No. PCT/US2015/059502, dated Dec. 23, 2015, 10 pages.
Russian Search Report issued in Russian Application No. 2017119064, dated Jun. 3, 2019, 4 pages (2 pages of English Translation and 2 pages of Foreign Language).
Russian Search Report issued in Russian Application No. 2017119065, dated Jun. 5, 2019, 4 pages (2 pages of English Translation & 2 pages of Foreign Language).
Russian Search Report issued in Russian Application No. 2017119066, dated Jun. 7, 2019, 4 pages (2 pages of English Translation & 2 pages of Foreign language).
Anestis et al. (Jun. 2018) "Current Advances of Targeting HGF/c-Met Pathway in Gastric Cancer", Annals of Translational Medicine, 6(12):10 pages.
Balla et al. (Jul. 2013) "Phosphoinositides: Tiny Lipids with Giant Impact on Cell Regulation", Physiological Reviews, 93(3):1019-1137.
Bryant et al. (Apr. 2019) "Combination of ERK and Autophagy Inhibition as a Treatment Approach for Pancreatic Cancer", Nature Medicine, 25(4):628-640 (53 pages).
Burakoff et al. (Jul. 2006) "A Phase 1/2a Trial of Sta 5326, an Oral Interleukin-12/23 Inhibitor, in Patients with Active Moderate to Severe Crohn's Disease", Inflammatory Bowel Diseases, 12(7):558-565.
Chong et al., (Jul. 2011) "Cardiovascular Disease and Mtor Signaling", Trends Cardiovascular Medicine, 21(5):151-155.
Chou Ting-Chao (Jan. 12, 2010) "Drug Combination Studies and Their Synergy Quantification Using the Chou-Talalay Method", Cancer Research, 70(2):440-446.
Choueiri et al. (Nov. 2014) "Pd-I1 Expression in Nonclear-cell Renal Cell Carcinoma", Annals of Oncology, 25(11):2178-2184.
Cross Ryan (Jun. 3, 2019) "Adjusting the Yin and Yang of the Cell", Chemical & Engineering Data, 97(22):35-39.
Dankner et al. (Mar. 15, 2018) "Classifying BRAF Alterations in Cancer: New Rational Therapeutic Strategies for Actionable Mutations", Oncogene, 37(24):3183-3199.
Dibble et al. (Aug. 24, 2012) "TBC1D7 is a Third Subunit of the TSC1-TSC2 Complex Upstream of mTorC1", Molecular Cell, 47(4):535-546.
Dorard et al. (Feb. 15, 2017) "Deciphering the RAS/ERK Pathway in Vivo", Biochemical Society Transactions, 45(1):27-36.
Duvallet et al. (Nov. 2011) "Interleukin-23: A Key Cytokine in Inflammatory Diseases", Annals of Medicine, 43(7):503-511.
Eden et al. (Feb. 2009) "Down-regulation of Epidermal Growth Factor Receptor Signalling Within Multivesicular Bodies", Biochemical Society Transactions, 37(Pt 1): 173-177.
Edkins et al. (Aug. 2006) "Recurrent KRAS Codon 146 Mutations in Human Colorectal Cancer", Cancer Biology & Therapy, 5(8):928-932.
Elder et al. (Jul. 2010) "The Utility of Sulfonate Salts in Drug Development", Journal of Pharmaceutical Sciences, 99(7):2948-2961.
Er et al. (Jun. 2013) "AKT Facilitates EGFR Trafficking and Degradation by Phosphorylating and Activating PIKfyve", Science Signaling, ra45, 6(279):13 pages.
Feldman et al. (Feb. 10, 2009) "Active-site Inhibitors of mTor Target Rapamycin-Yesistant Outputs of mTORC1 and mTORC2", PLoS Biology, e1000038, 7(2):13 pages.
Foster et al. (Apr. 11, 2016) "Activation Mechanism of Oncogenic Deletion Mutations in BRAF, EGFR, and HER2", Cancer Cell, 29(4):477-493.
Frampton et al. (Aug. 2015) "Activation of MET via Diverse Exon 14 Splicing Alterations Occurs in Multiple Tumor Types and Confers Clinical Sensitivity to MET Inhibitors", Cancer Discovery, 5(8):850-859.
Gayle et al. (Apr. 14, 2017) "B-cell Non-Hodgkin Lymphoma: Selective Vulnerability to PIKFYVE Inhibition", Autophagy, 13(6):1082-1083.
Gayle et al. (Mar. 30, 2017) "Identification of Apilimod as a First-in-class PIKfyve Kinase Inhibitor for Treatment of B-cell Non-Hodgkin Lymphoma", Blood, 129(13):1768-1778.

(56) References Cited

OTHER PUBLICATIONS

Gomez Manuel R. (1991) "Phenotypes of the Tuberous Sclerosis Complex with a Revision of Diagnostic Criteria", Annals of the New York Academy of Sciences, 615:1-7.
Grothey et al. (Jan. 26, 2013) "Regorafenib Monotherapy for Previously Treated Metastatic Colorectal Cancer (CORRECT): An International, Multicentre, Randomised, Placebo-Controlled, Phase 3 Trial", The Lancet, 381(9863):303-312.
Guo et al. (Mar. 1, 2011) "Activated Ras Requires Autophagy to Maintain Oxidative Metabolism and Tumorigenesis", Genes & Development, 25(5):460-470.
Harrison et al. (Jul. 2015) "Renal Cell Carcinoma Presenting with Paraneoplastic Hallucinations and Cognitive Decline from Limbic Encephalitis", Journal of General Internal Medicine, 30(7):1037-1040.
Hobbs et al. (2016) "RAS Isoforms and Mutations in Cancer at a Glance", Journal of Cell Science, 129(7):1287-1292.
Hobbs et al. (Mar. 2016) "Selective Targeting of the KRAS G12C Mutant: Kicking KRAS When It's Down", Cancer Cell, 29(3):251-253.
Hu et al. (Nov. 29, 2018) "Mutational Landscape of Secondary Glioblastoma Guides MET-Targeted Trial in Brain Tumor", Cell, 175(6):1665-1678 (33 pages).
Huang et al. (Jul. 2019) "The HGF-MET Axis Coordinates Liver Cancer Metabolism and Autophagy for Chemotherapeutic Resistance", Autophagy, 15(7):1258-1279.
Inokuchi et al. (Nov. 15, 2015) "Clinical Significance of MET in Gastric Cancer", World Journal of Gastrointestinal Oncology, 7(11):317-327.
Janes et al. (Jan. 25, 2018) "Targeting KRAS Mutant Cancers with a Covalent G12C-Specific Inhibitor", Cell, 172(3):578-589 (30 pages).
Jefferies et al. (Feb. 2008) "A Selective PIKfyve Inhibitor Blocks PtdIns(3,5)P2 Production and Disrupts Endomembrane Transport and Retroviral Budding", EMBO Reports, 9(2):164-170.
Johansson et al. (May 2014) "BRAF Inhibitors in Cancer Therapy", Pharmacology & Therapeutics, 142(2):176-182.
Jordon et al. (2012) "Vemurafenib for the Treatment of Melanoma", Expert Opinion on Pharmacotherapy, 13(17):2533-2543.
Kantola et al. (Nov. 6, 2012) "Stage-Dependent Alterations of the Serum Cytokine Pattern in Colorectal Carcinoma", British Journal of Cancer, 107(10):1729-1736.
Katiyar et al. (Nov. 1, 2007) "Interleukin-12 and Photocarcinogenesis", Toxicology and Applied Pharmacology, 224(3):220-227.
Kholodov et al. (1985) "Klinicheskaya Farmakokinetika", Meditsina, 26 pages.
Kidger et al. (Jul. 2018) "ERK1/2 inhibitors: New weapons to Inhibit the RAS-regulated RAF-MEK1/2-ERK1/2 Pathway", Pharmacology & Therapeutics, 187:45-60.
Kim et al. (Mar. 24, 2017) "Progress of Antibody-based Inhibitors of the HGF-cMET Axis in Cancer Therapy", Experimental & Molecular Medicine, e307, 49(3):7 pages.
Kim et al. (Oct. 1, 2007) "The Phosphoinositide Kinase PIKfyve Mediates Epidermal Growth Factor Receptor Trafficking to the Nucleus", Cancer Research, 67(19):9229-9237.
Kinsey et al. (Apr. 2019) "Protective Autophagy Elicited by RAF→MEK→ERK Inhibition Suggests a Treatment Strategy for RAS-driven Cancers", Nature Medicine, 25(4):620-627 (27 pages).
Labiris et al. (Dec. 2003) "Pulmonary Drug Delivery. Part II: The Role of Inhalant Delivery Devices and Drug Formulations in Therapeutic Effectiveness of Aerosolized Medications", British Journal of Clinical Pharmacology, 56(6):600-612.
Lan et al. (May 6, 2011) "IL-23/IL-23R: Potential Mediator of Intestinal Tumor Progression from Adenomatous Polyps to Colorectal Carcinoma", International Journal of Colorectal Disease, 26(12):1511-1518.
Langowski et al. (Jul. 27, 2006) "IL-23 Promotes Tumour Incidence and Growth", Nature, 442(7101):461-465.
Laplante et al. (2009) "mTor Signaling at a Glance", Journal of Cell Science, 3589-3594.
Lee et al. (Mar. 5, 2019) "MAP Kinase and Autophagy Pathways Cooperate to Maintain RAS Mutant Cancer Cell Survival", Proceedings of the National Academy of Sciences of the United States of America, 116(10):4508-4517.
Lin et al. (Feb. 2019) "Targeting Autophagy Potentiates Antitumor Activity of Met-TKIs Against Met-amplified Gastric Cancer", Cell Death & Disease, 10(2):11 pages.
Martin et al. (Mar. 27, 2013) "Inhibition of PIKfyve by YM-201636 Dysregulates Autophagy and Leads to Apoptosis-Independent Neuronal Cell Death", PLoS One, e60152, 8(3):14 pages.
Masliah-Planchon et al. (Jun. 21, 2016) "RAS-MAPK Pathway Epigenetic Activation in Cancer: miRNAs in Action", Oncotarget, 7(25):38892-38907.
Miranda et al., Sep. 2018, "Status of Agents Targeting the HGF/c-Met Axis in Lung Cancer", Cancers, 10(9):18 pages.
Mo et al. (Sep. 2017) "Targeting MET in cancer Therapy", Chronic Diseases and Translational Medicine, 3(3):148-153.
Nanzando (Jan. 16, 1998) "Dictionary of Medicine", 18th Edition, 13-14, 261 pages.
Ni et al. (Oct. 2019) "Drugging K-RasG12C through covalent inhibitors: Mission possible?", Pharmacology & Therapeutics, 202:49 pages.
Pal et al. (Aug. 2014 (e-published Jun. 26, 2014)) "Adjuvant Therapy for Renal Cell Carcinoma: Past, Present, and Future", The Oncologist, 19(8):851-859.
Pal et al., (Aug. 2013) "Adjuvant Therapy in Renal Cell Carcinoma—Past, Present, and Future", Seminars in Oncology, 40(4):482-491.
Palanisamy et al. (Jul. 2010) "Rearrangements of the RAF Kinase Pathway in Prostate Cancer, Gastric Cancer and Melanoma", Nature Medicine, 16(7):793-798 (13 pages).
Pant et al. (Oct. 2018) "Clinical Update on K-Ras Targeted Therapy in Gastrointestinal Cancers", Critical Reviews in Oncology/Hematology, 130:78-91 (36 pages).
Philips et al. (Oct. 16, 2014) "Therapeutic Uses of Anti-PD-1 and Anti-PD-L1 Antibodies", International Immunology, 27(1):39-46.
Pilotto et al. (Jan. 2017) "MET Exon 14 Juxtamembrane Splicing Mutations: Clinical and Therapeutical Perspectives for Cancer Therapy", Annals of Translational Medicine, 5(1):11 pages.
Rehman et al. (Mar. 2019) "MET Inhibition in Non-Small Cell Lung Cancer", European Medical Journal, 6(1):100-111.
Ritz et al. (Dec. 30, 2015) "Dose-Response Analysis Using R", PLoS One, e0146021, 10(12):13 pages.
Ryan et al. (Nov. 1, 2015) "Targeting RAS-mutant Cancers: is ERK the Key?", Trends Cancer, 1 (3):183-198 (26 pages).
Sakano Teruo (May 1991) "Chemotherapy of Malignant Lymphoma, with Special Regard to Non-Hodgkin's Lymphomas", International Journal of Hematology, 32(5):453-460 (11 pages).
Sergeev (1975) "A Short Course in Molecular Pharmacology", 1 page.
Seton-Rogers et al. (Apr. 1, 2019) "Eliminating Protective Autophagy in KRAS-mutant Cancers", Nature Reviews Cancer, 19:1 page.
Sharma et al. (Oct. 2015) "A Family of PIKfyve Inhibitors with Therapeutic Potential Against Autophagy-Dependent Cancer Cells Disrupt Multiple Events in Lysosome Homeostasis", Autophagy, 15(10):1694-1718.
Steadman (Feb. 20, 2002) "English-Japanese Medical Dictionary", 5th Edition, 3 pages.
Stephens et al. (2017) "Tumor RAS Gene Expression Levels are Influenced by the Mutational Status of RAS Genes and Both Upstream and Downstream RAS Pathway Genes", Cancer Informatics, 16:1-10.
Ting-Chao Chou (Jan. 2010) "Drug Combination Studies and Their Synergy Quantification Using the Chou-Talalay Method", Cancer Research, 70(2):440-446.
Tovar et al. (May 2017) "MET in Human Cancer: Germline and Somatic Mutations", Annals of Translational Medicine, 5(10):205-210.
Vengerovskiy (2003) "Pharmacological Incompatibility/ Bulletin of Siberian Medicine", 3:49-56.
Wang et al. (Dec. 19, 2012) "Implications of anti-cytokine therapy in colorectal cancer and autoimmune diseases", Annals of the Rheumatic Diseases, 72(Suppl 2):ii100-ii103.

(56) References Cited

OTHER PUBLICATIONS

White Eileen (Mar. 5, 2019) "Blockade of RAF and Autophagy is the One-two Punch to Take Out Ras", Proceedings of the National Academy of Sciences of the United States of America, 116(10):3965-3967.
Wolff et al. (1996) "Metabolic Considerations in Prodrug Design", Burger's Medicinal Chemistry and Drug Discovery. 5th edition, 1:949-982.
Wong Michael (Mar.-Apr. 2013) "Mammalian Target of Rapamycin (mTor) Pathways in Neurological Diseases", Biomedical Journal, 36(2):40-50.
Yaeger et al. (Mar. 2019) "Targeting Alterations in the RAF-MEK Pathway", Cancer Discovery, 9(3):329-341.
Young et al. (Jul. 1998) "The Genetic Basis of Tuberous Sclerosis", Molecular Medicine Today, 4(7):313-319.
Zhang et al. (Apr. 2016) "Regulation of the MET Oncogene: Molecular Mechanisms", Carcinogenesis, 37(4):345-355.
Aapro et al. (Sep. 1, 2006) "A Phase III, Double-Blind, Randomized Trial of Palonosetron Compared with Ondansetron in Preventing Chemotherapy-Induced Nausea and Vomiting Following Highly Emetogenic Chemotherapy", Annals of Oncology, 17(9):1441-1449.
Baird et al. (Jun. 19, 2013) "IL-23R is Epigenetically Regulated and Modulated by Chemotherapy in Non-Small Cell Lung Cancer", Frontiers in Oncology, 3(162):1-9.
Cai et al. (Jul. 25, 2013) "PIKfyve, a Class III PI Kinase, Is the Target of the Small Molecular IL-12/IL-23 Inhibitor Apilimod and a Player in Toll-like Receptor Signaling", Chemistry & Biology, 20(7):912-921.
Chou et al. (1984) "Quantitative Analysis of Dose-Effect Relationships: The Combined Effects of Multiple Drugs or Enzyme Inhibitors", Advances in Enzyme Regulation, 22:27-55.
Howe et al. (Jun. 1995) "Rodent Model of Reproductive Tract Leiomyomata. Establishment and Characterization of Tumor-Derived Cell Lines", The American Journal of Pathology, 146(6):1568-1579.
Krausz et al. (May 25, 2012) "A Phase IIa, Randomized, Double-Blind, Placebo-Controlled Trial of Apilimod Mesylate, an Interleukin-12/Interleukin-23 Inhibitor, in Patients With Rheumatoid Arthritis", Arthritis and Rheumatism, 64(6): 1750-1755.
Krausz et al. (Jun. 2012) "Brief Report: A Phase Iia, Randomized, Double-Blind, Placebo-Controlled Trial of Apilimod Mesylate, An Interleukin-12/Interleukin-23 Inhibitor, in Patients with Rheumatoid Arthritis", Arthritis & Rheumatology, 64(6): 1750-1755.
Laplante et al. (Apr. 13, 2012) "mTOR Signaling in Growth Control and Disease", Cell, 149(2):274-293.
Liu et al. (2009) "mTOR Mediated Anti-Cancer Drug Discovery", Drug Discovery Today Therapeutic Strategies, 6 (2):47-55.
Menon et al. (2009) "Common Corruption of the Mtor Signaling Network in Human Tumors", Oncogene, 27:S43-S51.
Michaelis et al. (Apr. 26, 2012) "Dabigatran and Dabigatran Ethyl Ester: Potent Inhibitors of Ribosyldihydronicotinamide Dehydrogenase (NQO2)", Journal of Medicinal Chemistry, 55(8):3934-3944.
Novero et al. (2014) "Ibrutinib for B cell malignancies", Experimental Hematology & Oncology, 3(4):7 pages.
Onda et al. (Sep. 1999) "Tsc2(+/−) Mice Develop Tumors in Multiple Sites that Express Gelsolin and are Influenced by Genetic Background", Journal of Clinical Investigation, 104(6):687-695.
Puls et al. (2011) "Current Status of Src Inhibitors in Solid Tumor Malignancies", The Oncologist, 16:566-578.
Sands et al. (Jul. 2010) "Randomized, Double-Blind, Placebo-Controlled Trial of the Oral Interleukin-12/23 Inhibitor Apilimod Mesylate for Treatment of Active Crohn's Disease", Inflammatory bowel disease, 16(7):1209-1218.
Wada et al. (Apr. 6, 2012) "Apilimod Inhibits the Production of IL-12 and IL-23 and Reduces Dendritic Cell Infiltration in Psoriasis", PLOS One, 7(4):e35069:1-10.
Wada et al. (Oct. 19, 2006) "Selective Abrogation of Th1 Response by STA-5326, a Potent IL-12/IL-23 Inhibitor", Blood, 109(3):1156-1164.
Zhang et al. (Oct. 2003) "Loss of Tsc1/Tsc2 Activates mTOR and Disrupts PI3K-Akt Signaling Through Downregulation of PDGFR", Journal of Clinical Investigation, 112(8): 1223-1233.
International Search Report mailed on Apr. 15, 2015 for International Application No. PCT/US2015/012733, filed on Jan. 23, 2015. 3 pages.
Extended European Search Report dated Sep. 5, 2017 for EP Application No. EP15740043.3, filed Jan. 23, 2015. 8 pages.
International Search Report and Written Opinion received for PCT Application No. PCT/US20/70522, dated Nov. 25, 2020, 13 pages.
Dutcher Janice P. (2013) "Recent Developments in The Treatment of Renal Cell Carcinoma", Therapeutic Advances in Urology, 5(6):338-353.
Kim et al. (Nov. 2016) "Targeting Cancer Metabolism by Simultaneously Disrupting Parallel Nutrient Access Pathways", The Journal of Clinical Investigation, 126(11):4088-4102.
Krishna et al. (Sep. 12, 2016) "PIKfyve Regulates Vacuole Maturation and Nutrient Recovery following Engulfment", Development Cell, 38(5):536-547.

Normal lung fibroblasts (WI-38) were seeded into 96 well plates. 24 h later, cells were treated with increasing concentrations of apilimod (19.5 - 10000nM) and cultured for an additional 72 h. Cell viability was determined using cell Titer-Glo® and cell viability was expressed percentage of the control (DMSO).

Kd = 75 pM

APILIMOD COMPOSITIONS AND METHODS FOR USING SAME

CROSS-REFERENCE TO RELATED APPLICATIONS

This application is a continuation applicatin to U.S. patent application Ser. No. 16/193,045, filed Nov. 16, 2018, now abandoned, which is a continuation application to U.S. patent application Ser. No. 15/113,154, filed Jul. 21, 2016, now U.S. Pat. No. 10,179,135 issued on Jan. 15, 2019, which is a national stage application filed under 35 U.S.C. § 371, of International Patent Application No. PCT/US2015/012733, filed Jan. 23, 2015, which claims the benefit of and priority to U.S. Provisional Patent Application No. 62/077,127, filed Nov. 7, 2014, U.S. Provisional Patent Application No. 61/931,078, filed Jan. 24, 2014, and U.S. Provisional Patent Application No. 61/931,075, filed Jan. 24, 2014, the contents of each of which are incorporated herein by reference in their entireties.

FIELD OF THE INVENTION

The present invention relates to compositions comprising apilimod and methods of using same.

BACKGROUND OF THE INVENTION

Apilimod, also referred to as STA-5326, hereinafter "apilimod", is recognized as a potent transcriptional inhibitor of IL-12 and IL-23. See e.g., Wada et al. *Blood* 109 (2007): 1156-1164. IL-12 and IL-23 are inflammatory cytokines normally produced by immune cells, such as B-cells and macrophages, in response to antigenic stimulation. Autoimmune disorders and other disorders characterized by chronic inflammation are characterized in part by inappropriate production of these cytokines. In immune cells, the selective inhibition of IL-12/IL-23 transcription by apilimod was recently shown to be mediated by apilimod's direct binding to phosphatidylinositol-3-phosphate 5-kinase (PIKfyve). See, e.g., Cal et al. *Chemistry and Biol.* 20 (2013):912-921. PIKfyve plays a role in Toll-like receptor signaling, which is important in innate immunity.

Based upon its activity as an immunomodulatory agent and a specific inhibitor of IL-12/IL-23, apilimod has been proposed as useful in treating autoimmune and inflammatory diseases and disorders. See e.g., U.S. Pat. Nos. 6,858,606 and 6,660,733 (describing a family of pyrimidine compounds, including apilimod, purportedly useful for treating diseases and disorders characterized by IL-12 or IL-23 overproduction, such as rheumatoid arthritis, sepsis, Crohn's disease, multiple sclerosis, psoriasis, or insulin dependent diabetes mellitus). Similarly, apilimod was suggested to be useful for treating certain cancers based upon its activity to inhibit c-Rel or IL-12/23, particularly in cancers where these cytokines were believed to play a role in promoting aberrant cell proliferation. See e.g., WO 2006/128129 and Baird et al., *Frontiers in Oncology* 3:1 (2013, respectively).

Each of three clinical trials of apilimod has focused on its potential efficacy in autoimmune and inflammatory diseases. The trials were conducted in patients having psoriasis, rheumatoid arthritis, and Crohn's disease. An open label clinical study in patients with psoriasis concluded that oral administration of apilimod showed immunomodulatory activity supporting the inhibition of IL-12/IL-23 synthesis for the treatment of TH1- and TH17-mediated inflammatory diseases. Wada et al., *PLosOne* 7:e35069 (April 2012). But the results of controlled trials in rheumatoid arthritis and Crohn's disease did not support the notion that IL-12/IL-23 inhibition by apilimod translates into clinical improvement in either of these indications. In a randomized, double-blind, placebo-controlled Phase II clinical trial of apilimod in patients with rheumatoid arthritis, apilimod failed to alter synovial IL-12 and IL-23 expression. Krauz et al., *Arthritis & Rheumatism* 64:1750-1755 (2012). The authors concluded that the "results do not support the notion the IL-12/IL-23 inhibition by apilimod is able to induce robust clinical improvement in RA." Similarly, a randomized, double-blind, placebo-controlled trial of apilimod for treatment of active Crohn's disease concluded that, although well tolerated, apilimod did not demonstrate efficacy over placebo. Sands et al *Inflamm Bowel Dis.* 2010 July; 16(7): 1209-18.

The mammalian target of rapamycin (mTOR) pathway is an important cellular signaling pathway that is involved in multiple physiological functions, including cell growth, cell proliferation, metabolism, protein synthesis, and autophagy (La Plante et al *Cell* 2012, (149 (2), pp. 274-293). mTOR is a kinase that integrates intracellular and extracellular cues that signal the levels of amino acids, stress, oxygen, energy, and growth factors and regulates the cellular response to these environment cues. mTOR deregulation has been implicated in a wide range of disorders and diseases, including cancer, obesity, diabetes, and neurodegeneration. Certain components of the mTOR pathway have been explored as drug targets for treating some of these diseases. However, therapeutic efficacy has been limited, for example, in the treatment of some cancers, and some mTOR inhibitors have been shown to have an adverse effect on metabolism. The tuberous sclerosis complex tumor suppressor genes, TSC1 and TSC2, are negative regulators of mTOR.

SUMMARY OF THE INVENTION

The present invention is based in part on the surprising discovery that apilimod is a highly cytotoxic agent in TSC null cells. In these cells, the mTOR pathway is constitutively active. The mTOR pathway is activated in a number of cancers, and in further screening of over 100 cancer cell lines apilimod showed anti-proliferative activity in cell lines from diverse cancers. Among the apilimod sensitive cancer cell lines, B-cell lymphomas were the most sensitive. But, unexpectedly, the differential sensitivity of B cell lymphomas to apilimod did not correlate with c-Rel expression, IL-12 expression, or IL-23 expression in these cells. This was surprising because earlier work had suggested apilimod would be useful against cancers where c-Rel and/or IL-12/23 expression were critical in promoting aberrant cell proliferation. Instead, the present inventors demonstrated that apilimod's cytotoxic activity in cancer cells was due to an inhibition of intracellular trafficking and a corresponding increase in apoptosis. This activity was not predicted based upon apilimod's immunomodulatory activity via its inhibition of IL-12/23 production. In addition, a screen of over 450 kinases identified PIKfyve as the only high affinity binding target (Kd=75 pM) for apilimod in a human cancer cell line. The present invention provides new methods for the therapeutic use of apilimod, especially in treating cancer, and particularly in treating B cell lymphomas, and especially those that are resistant or refractory to standard chemotherapy regimens.

In one aspect, the present invention provides a method for treating cancer in a subject in need thereof, the method comprising administering to the subject a therapeutically effective amount of an apilimod composition of the invention, said composition comprising apilimod, or a pharmaceutically acceptable salt, solvate, clathrate, hydrate, polymorph, prodrug, analog or derivative thereof. In one embodiment, the apilimod composition comprises apilimod free base or apilimod dimesylate. In one embodiment, the method further comprises administering at least one additional active agent to the subject. The at least one additional active agent may be a therapeutic agent or a non-therapeutic agent. The at least one additional active agent may be administered in a single dosage form with the apilimod composition, or in a separate dosage form from the apilimod composition. In one embodiment, the at least one additional active agent is selected from the group consisting of an alkylating agent, an intercalating agent, a tublin binding agent, a corticosteroid, and combinations thereof. In one embodiment, the at least one additional active agent is a therapeutic agent selected from the group consisting of ibrutinib, rituximab, doxorubicin, prednisolone, vincristine, velcade, and everolimus, and combinations thereof. In one embodiment, the at least one additional active agent is a therapeutic agent selected from cyclophosphamide, hydroxydaunorubicin (also referred to as doxorubicin or Adriamycin™), vincristine (also referred to as Oncovin™) prednisone, prednisolone, and combinations thereof. In one embodiment, the at least one additional active agent is a non-therapeutic agent selected to ameliorate one or more side effects of the apilimod composition. In one embodiment, the non-therapeutic agent is selected from the group consisting of ondansetron, granisetron, dolasetron and palonosetron. In one embodiment, the non-therapeutic agent is selected from the group consisting of pindolol and risperidone.

In one embodiment, the dosage form of the apilimod composition is an oral dosage form. In another embodiment, the dosage form of the apilimod composition is suitable for intravenous administration. In one embodiment, where the dosage form is suitable for intravenous administration, administration is by a single injection or by a drip bag.

In one embodiment, the subject is a human cancer patient. In one embodiment, the human cancer patient in need of treatment with an apilimod composition of the invention is one whose cancer is refractory to a standard chemotherapy regimen. In one embodiment, the human cancer patient in need of treatment with an apilimod composition is one whose cancer has recurred following treatment with a standard chemotherapy regimen. In one embodiment, the cancer is a lymphoma. In one embodiment, the cancer is a B cell lymphoma. In one embodiment, the B cell lymphoma is a non-Hodgkin's B cell lymphoma. In one embodiment, the non-Hodgkin's B cell lymphoma is selected from a diffuse large B cell lymphoma (DLBCL), a Burkitt's lymphoma, a mediastinal B cell lymphoma, a mantle cell lymphoma, and a follicular lymphoma. In one embodiment, the non-Hodgkin's B cell lymphoma is DLBCL. In one embodiment, the DLBCL is the GCB subtype.

In one embodiment, the standard chemotherapy regimen comprises one or more therapeutic agents selected from the group consisting of ibrutinib, rituximab, doxorubicin, prednisolone, vincristine, velcade, cyclophoamide, dexamethasone and everolimus. In one embodiment, the standard chemotherapy regimen is selected from CHOP, (cyclophosphamide, hydroxydaunorubicin, Oncovin™ (vincristine), and prednisone or prednisolone), COOP (cyclophosamide, vincristine sulfate, procarbazine hydrochloride, prednisone), CVP (cyclophosamide, vincristine sulfate, prednisone), EPOCH (etoposide, prednisone, vincristine sulfate, cyclophosphamide, doxorubicin hydrochloride), Hyper-CVAD (cyclophosphamide, vincristine sulfate, doxorubicin hydrochloride, dexamethasone), ICE (ifosfamide, carboplatin, etoposide), R-CHOP (rituximab, cyclophosamide, vincristine sulfate, procarbazine hydrochloride, prednisone, and R-CVP (rituximab, cyclophosamide, vincristine sulfate, prednisone).

In one embodiment, the method is a method of treating a lymphoma using a combination therapy comprising an apilimod composition and a chemotherapy regimen for the treatment of the lymphoma. In one embodiment, the chemotherapy regimen is the CHOP regimen. In another embodiment, the chemotherapy regimen is selected from COOP, CVP, EPOCH, Hyper-CVAD, ICE, R-CHOP, and R-CVP.

In some embodiments, apilimod compositions are provided herein that are useful for treating cancers associated with TSC deficiency and/or mTOR activation. In some embodiments, methods are provided herein for treating TSC1- or TSC2-deficient cancers using an apilimod composition. In some embodiments, methods are provided for treating mTOR associated cancers using an apilimod composition. In some embodiments, an mTOR associated cancer is associated with a deletion, loss of function mutation, low expression or other TSC1 or TSC2 deficiency. In some embodiments, an mTOR associated cancer is associated with a gain of function mutation that results in activation (e.g., constitutive activation) of mTOR pathway activity in cells of the cancer. In some embodiments, methods are provided herein that further involve determining whether a subject having cancer is a candidate for treatment with an apilimod composition based on the TSC1, TSC2 and/or mTOR status of the subject. For example, in some embodiments, a subject having a TSC1 or TSC2 deficiency (e.g., an inactivating mutation in TSC1 or TSC2) or constitutively active mTOR signaling is a candidate for treatment with an apilimod composition.

DETAILED DESCRIPTION OF THE INVENTION

Figure 1:
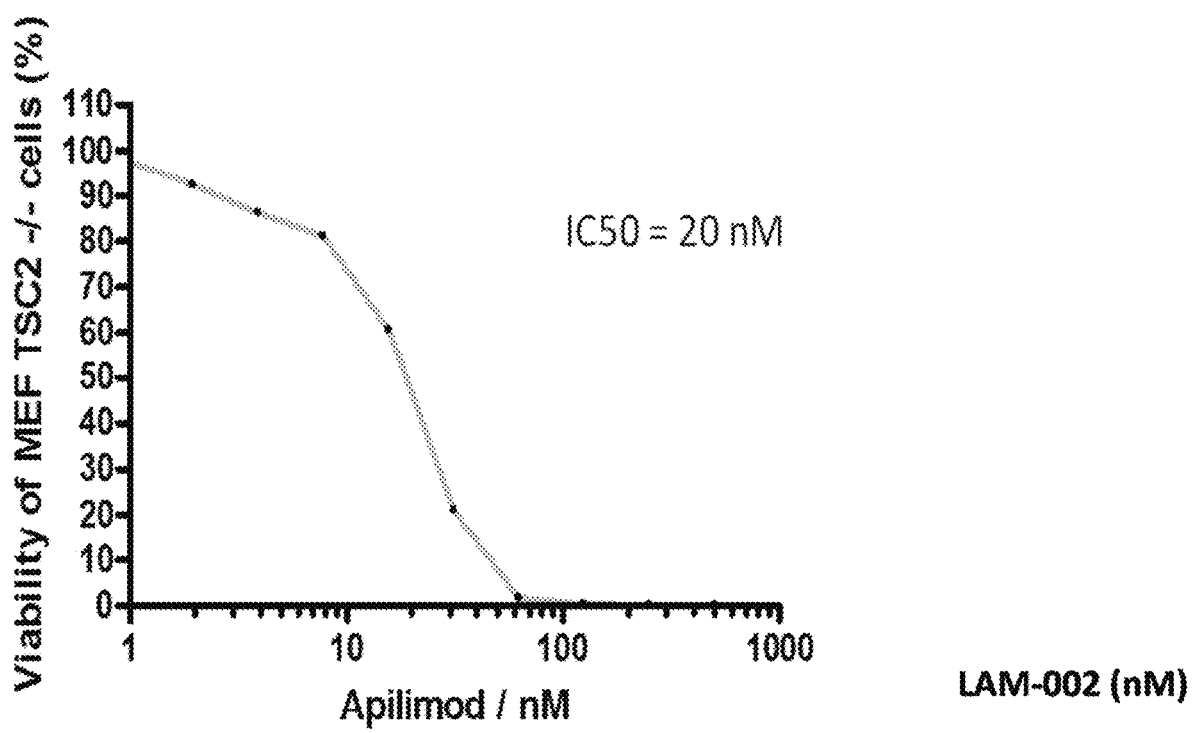
FIG. 1: TSC2 deficient cells are highly sensitive to apilimod ($IC_{50}$=20 nM).

The present invention provides compositions and methods related to the use of apilimod for treating cancer in a subject, preferably a human subject, in need of such treatment. The present invention generally relates to new uses of apilimod based upon the surprising discovery of apilimod's cytotoxic activity against a range of cancer cells of both lymphoid and non-lymphoid origin, an activity that is not clearly related to, or predictable from, apilimod's known immunomodulatory and IL-12/23 inhibitory activity. In addition, the present invention provides novel therapeutic approaches to cancer treatment based upon combination therapy utilizing apilimod and at least one additional therapeutic agent. The combination therapies described herein exploit the unique cytotoxic activity of apilimod which is shown to provide a synergistic effect when combined with other therapeutic agents, including for example, anti-cancer agents.

As used herein, the term "an apilimod composition" may refer to a composition comprising apilimod itself (free base), or may encompass pharmaceutically acceptable salts, solvates, clathrates, hydrates, polymorphs, prodrugs, analogs or derivatives of apilimod, as described below. The structure of apilimod is shown in Formula I:

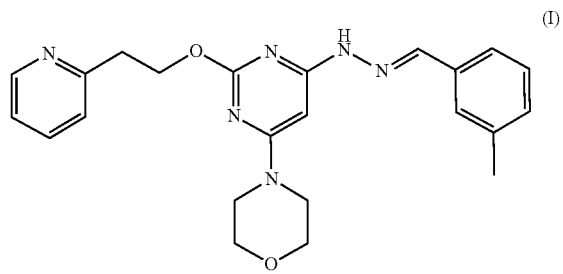

The chemical name of apilimod is 2-[2-Pyridin-2-yl)-ethoxy]-4-N'-(3-methyl-benzilidene)-hydrazino]-6-(morpholin-4-yl)-pyrimidine (IUPAC name: (E)-4-(6-(2-(3-methylbenzylidene)hydrazinyl)-2-(2-(pyridin-2-yl)ethoxy) pyrimidin-4-yl)morpholine), and the CAS number is 541550-19-0.

Apilimod can be prepared, for example, according to the methods described in U.S. Pat. Nos. 7,923,557, and 7,863,270, and WO 2006/128129.

As used herein, the term "pharmaceutically acceptable salt," is a salt formed from, for example, an acid and a basic group of an apilimod composition. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, besylate, gentisinate, fumarate, gluconate, glucaronate, saccharate, formate, benzoate, glutamate, methanesulfonate, ethanesulfonate, benzenesulfonate, p-toluenesulfonate, and pamoate (e.g., 1,1'-methylene-bis-(2-hydroxy-3-naphthoate)) salts. In a preferred embodiment, the salt of apilimod comprises methanesulfonate.

The term "pharmaceutically acceptable salt" also refers to a salt prepared from an apilimod composition having an acidic functional group, such as a carboxylic acid functional group, and a pharmaceutically acceptable inorganic or organic base.

The term "pharmaceutically acceptable salt" also refers to a salt prepared from an apilimod composition having a basic functional group, such as an amino functional group, and a pharmaceutically acceptable inorganic or organic acid.

The salts of the compounds described herein can be synthesized from the parent compound by conventional chemical methods such as methods described in Pharmaceutical Salts: Properties, Selection, and Use, P. Hemrich Stalil (Editor), Camille G. Wermuth (Editor), ISBN: 3-90639-026-8, August 2002. Generally, such salts can be prepared by reacting the parent compound with the appropriate acid in water or in an organic solvent, or in a mixture of the two.

One salt form of a compound described herein can be converted to the free base and optionally to another salt form by methods well known to the skilled person. For example, the free base can be formed by passing the salt solution through a column containing an amine stationary phase (e.g. a Strata-NH$_2$ column). Alternatively, a solution of the salt in water can be treated with sodium bicarbonate to decompose the salt and precipitate out the free base. The free base may then be combined with another acid using routine methods.

As used herein, the term "polymorph" means solid crystalline forms of a compound of the present invention (e.g., 2-[2-Pyridin-2-yl)-ethoxy]-4-N'-(3-methyl-benzilidene)-hydrazino]-6-(morpholin-4-yl)-pyrimidine) or complex thereof. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

As used herein, the term "hydrate" means a compound of the present invention (e.g., 2-[2-Pyridin-2-yl)-ethoxy]-4-N'-(3-methyl-benzilidene)-hydrazino]-6-(morpholin-4-yl)-pyrimidine) or a salt thereof, which further includes a stoichiometric or non-stoichiometric amount of water bound by non-covalent intermolecular forces.

As used herein, the term "clathrate" means a compound of the present invention (e.g., 2-[2-Pyridin-2-yl)-ethoxy]-4-N'-(3-methyl-benzilidene)-hydrazino]-6-(morpholin-4-yl)-pyrimidine) or a salt thereof in the form of a crystal lattice that contains spaces (e.g., channels) that have a guest molecule (e.g., a solvent or water) trapped within.

As used herein, the term "prodrug" means a derivative of a compound described herein (e.g., 2-[2-Pyridin-2-yl)-ethoxy]-4-N'-(3-methyl-benzilidene)-hydrazino]-6-(morpholin-4-yl)-pyrimidine) that can hydrolyze, oxidize, or otherwise react under biological conditions (in vitro or in vivo) to provide a compound of the invention. Prodrugs may only become active upon such reaction under biological conditions, or they may have activity in their unreacted forms. Examples of prodrugs contemplated in this invention include, but are not limited to, analogs or derivatives of a compound described herein (e.g., 2-[2-Pyridin-2-yl)-ethoxy]-4-N'-(3-methyl-benzilidene)-hydrazino]-6-(morpholin-4-yl)-pyrimidine) that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds of any one of the formulae disclosed herein that comprise —NO, —NO$_2$, —ONO, or —ONO$_2$ moieties. Prodrugs can typically be prepared using well-known methods, such as those described by Burger's Medicinal Chemistry and Drug Discovery (1995) 172-178, 949-982 (Manfred E. Wolff ed., 5th ed).

As used herein, the term "solvate" or "pharmaceutically acceptable solvate," is a solvate formed from the association of one or more solvent molecules to one of the compounds disclosed herein (e.g., 2-[2-Pyridin-2-yl)-ethoxy]-4-N'-(3-methyl-benzilidene)-hydrazino]-6-(morpholin-4-yl)-pyrimidine). The term solvate includes hydrates (e.g., hemi-hydrate, mono-hydrate, dihydrate, trihydrate, tetrahydrate, and the like).

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound. As used herein, the term "derivative" refers to compounds that have a common core structure, and are substituted with various groups as described herein.

Methods of Treatment

The present invention provides methods for the treatment of cancer in a subject in need thereof by administering to the subject a therapeutically effective amount of an apilimod composition of the invention, said composition comprising apilimod, or a pharmaceutically acceptable salt, solvate, clathrate, hydrate, polymorph, prodrug, analog or derivative thereof. In one embodiment, the apilimod composition comprises apilimod free base or apilimod dimesylate. The present invention further provides the use of an apilimod composition for the preparation of a medicament useful for the treatment of cancer.

In one embodiment, the cancer is brain cancer, glioma, sarcoma, breast cancer, lung cancer, non-small-cell lung cancer, mesothelioma, appendiceal cancer, genitourinary cancers, renal cell carcinoma, prostate cancer, bladder cancer, testicular cancer, penile cancer, cervical cancer, ovarian cancer, von Hippel Lindau disease, head and neck cancer, gastrointestinal cancer, hepatocellular carcinoma, gallbladder cancer, esophageal cancer, gastric cancer, colorectal cancer, pancreatic cancer, neuroendocrine tumors, thyroid tumor, pituitary tumor, adrenal tumor, hematological malignancy, or leukemia.

In one embodiment the cancer is a lymphoma. In one embodiment, the lymphoma is a B cell lymphoma. In one embodiment, the B cell lymphoma is selected from the group consisting of a Hodgkin's B cell lymphoma and a non-Hodgkin's B cell lymphoma. In one embodiment, the B cell lymphoma is a non-Hodgkin's B cell lymphoma selected from the group consisting of DLBCL, follicular lymphoma, marginal zone lymphoma (MZL) or mucosa associated lymphatic tissue lymphoma (MALT), small cell lymphocytic lymphoma (overlaps with chronic lymphocytic leukemia) and mantle cell lymphoma. In one embodiment, the B cell lymphoma is a non-Hodgkin's B cell lymphoma selected from the group consisting of Burkitt lymphoma, Burkitt lymphoma, Primary mediastinal (thymic) large B-cell lymphoma, Lymphoplasmacytic lymphoma, which may manifest as Waldenström macroglobulinemia, Nodal marginal zone B cell lymphoma (NMZL), Splenic marginal zone lymphoma (SMZL), Intravascular large B-cell lymphoma, Primary effusion lymphoma, Lymphomatoid granulomatosis, T cell/histiocyte-rich large B-cell lymphoma, Primary central nervous system lymphoma, Primary cutaneous diffuse large B-cell lymphoma, leg type (Primary cutaneous DLBCL, leg type), EBV positive diffuse large B-cell lymphoma of the elderly, Diffuse large B-cell lymphoma associated with inflammation, Intravascular large B-cell lymphoma, ALK-positive large B-cell lymphoma, and Plasmablastic lymphoma.

Combination Therapy

The present invention also provides methods comprising combination therapy. As used herein, "combination therapy"

or "co-therapy" includes the administration of a therapeutically effective amount of an apilimod composition with at least one additional active agent, as part of a specific treatment regimen intended to provide a beneficial effect from the co-action of the apilimod composition and the additional active agent. "Combination therapy" is not intended to encompass the administration of two or more therapeutic compounds as part of separate monotherapy regimens that incidentally and arbitrarily result in a beneficial effect that was not intended or predicted.

In one embodiment, the method is a method of treating cancer using a combination therapy comprising an apilimod composition and a chemotherapy regimen for the treatment of cancer. In one embodiment, the chemotherapy regimen is the CHOP regimen. CHOP refers to a regimen generally used in the treatment of non-Hodgkin's lymphoma consisting of the following active agents: (C)yclophosphamide, an alkylating agent which damages DNA by binding to it and causing the formation of cross-links; (H)ydroxydaunorubicin (also called doxorubicin or Adriamycin), an intercalating agent which damages DNA by inserting itself between DNA bases; (O)ncovin (vincristine), which prevents cells from duplicating by binding to the protein tubulin; and (P)rednisone or (P)rednisolone, which are corticosteroids. In another embodiment, the chemotherapy regimen is selected from COOP (cyclophosamide, vincristine sulfate, procarbazine hydrochloride, prednisone), CVP (cyclophosamide, vincristine sulfate, prednisone), EPOCH (etoposide, prednisone, vincristine sulfate, cyclophosphamide, doxorubicin hydrochloride), Hyper-CVAD (cyclophosphamide, vincristine sulfate, doxorubicin hydrochloride, dexamethasone), ICE (ifosfamide, carboplatin, etoposide), R-CHOP (rituximab, cyclophosamide, vincristine sulfate, procarbazine hydrochloride, prednisone, and R-CVP (rituximab, cyclophosamide, vincristine sulfate, prednisone).

The at least one additional active agent may be a therapeutic agent, for example an anti-cancer agent or a cancer chemotherapeutic agent, or a non-therapeutic agent, and combinations thereof. With respect to therapeutic agents, the beneficial effect of the combination includes, but is not limited to, pharmacokinetic or pharmacodynamic co-action resulting from the combination of therapeutically active compounds. With respect to non-therapeutic agents, the beneficial effect of the combination may relate to the mitigation of a toxicity, side effect, or adverse event associated with a therapeutically active agent in the combination.

In one embodiment, the at least one additional agent is a non-therapeutic agent which mitigates one or more side effects of an apilimod composition, the one or more side effects selected from any of nausea, vomiting, headache, dizziness, lightheadedness, drowsiness and stress. In one aspect of this embodiment, the non-therapeutic agent is an antagonist of a serotonin receptor, also known as 5-hydroxytryptamine receptors or 5-HT receptors. In one aspect, the non-therapeutic agent is an antagonist of a $5-HT_3$ or $5-HT_{1a}$ receptor. In one aspect, the non-therapeutic agent is selected from the group consisting of ondansetron, granisetron, dolasetron and palonosetron. In another aspect, the non-therapeutic agent is selected from the group consisting of pindolol and risperidone.

In one embodiment, the at least one additional agent is a therapeutic agent. In one embodiment, the therapeutic agent is an anti-cancer agent. In one embodiment, the anti-cancer agent is ibrutinib. In one embodiment, an apilimod composition is administered along with ibrutinib in a single dosage form or in separate dosage forms. In one embodiment, the dosage form is an oral dosage form. In another embodiment, the dosage form is suitable for intravenous administration.

In one embodiment, the anti-cancer agent is a drug that is approved for use in treating lymphoma. Non-limiting examples of such drugs include abitrexate (methotrexate), adcetris (brentuximab vedotin), ambochlorin (chlorambucil), amboclorin (chloramucil), arranon (nelarabine), becenum (carmustine), beleodaq (belinostat), belinostat, bendamustine hydrochloride, bexxar (tositumomab and Iodine I 131 tositumomab), BiCNU (carmustine), blenoxane (bleomycin), bleomycin, bortezomib, brentuximab vedotin, carmubris (carmustine), carmustine, chlorambucil, clafen (cyclophosphamide), cyclophosphamide, cytoxan (cyclophosphamide), denileukin diftitox, DepoCyt (liposomal cytarabine), doxorubicin hydrochloride, folex (methotrexate), folotyn (pralatrexate), ibritumomab tiuxetan, ibrutinib, idelalisib, imbruvica (ibtrutinib), intron A (recombinant interferon Alfa-2b), istodax (romidepsin), lenalidomide, leukeran (chlorambucil), linfolizin (chlorambucil), liposomal cytarabine, mechlorethamine hydrochloride, methotrexate, methotrexate LPF (methotrexate), mexate (methotrexate), mexate-AQ (methotrexate), mozobil (perixafor), mustargen (mechlorethamine hydrochloride), nelarabine, neosar (cyclophosphamide), ontak (denifleukin diftitox), perixafor, pralatrexate, prednisone, recombinant interferon Alfa-2b, revlimid (lenalidomide), rituxan (rituximab), rituximab, romidepsin, tositumomab and iodine I 131 tositumomab, treanda (bendamustine hydrochloride), velban (vinblastine sulfate), velcade (bortezomib), velsar (vinblasinte sulfate), vinblastine sulfate, vincasar PFS (vincristine sulfate), vincristine sulfate, vorinostat, zevalin (ibritumomab triuxetan), zolinza (vorinostat), and zydelig (idelalisib).

In one embodiment, the anti-cancer agent is selected from an inhibitor of EZH2, e.g., EPZ-6438. In one embodiment, the anti-cancer agent is selected from taxol, vincristine, doxorubicin, temsirolimus, carboplatin, ofatumumab, rituximab, and combinations thereof.

In one embodiment, the at least one additional agent is a B cell receptor pathway inhibitor. In some embodiments, the B cell receptor pathway inhibitor is a CD79A inhibitor, a CD79B inhibitor, a CD 19 inhibitor, a Lyn inhibitor, a Syk inhibitor, a PI3K inhibitor, a Blnk inhibitor, a PLCy inhibitor, a PKCP inhibitor, or a combination thereof. In some embodiments, the at least one additional agent is an antibody, B cell receptor signaling inhibitor, a PI3K inhibitor, an IAP inhibitor, an mTOR inhibitor, a radioimmunotherapeutic, a DNA damaging agent, a proteosome inhibitor, a histone deacetylase inhibitor, a protein kinase inhibitor, a hedgehog inhibitor, an Hsp90 inhibitor, a telomerase inhibitor, a Jak1/2 inhibitor, a protease inhibitor, a PKC inhibitor, a PARP inhibitor, or a combination thereof.

In one embodiment, the at least one additional agent is selected from chlorambucil, ifosphamide, doxorubicin, mesalazine, thalidomide, lenalidomide, temsirolimus, everolimus, fludarabine, fostamatinib, paclitaxel, docetaxel, ofatumumab, rituximab, dexamethasone, prednisone, CAL-101, ibritumomab, tositumomab, bortezomib, pentostatin, endostatin, or a combination thereof.

In one embodiment, the at least one additional agent is a monoclonal antibody such as, for example, alemtuzumab, bevacizumab, catumaxomab, cetuximab, edrecolomab, gemtuzumab, ofatumumab, panitumumab, rituximab, trastuzumab, eculizumab, efalizumab, muromab-CD3, natalizumab, adalimumab, afelimomab, certolizumab pegol, golimumab, infliximab, basiliximab, canakinumab, daclizumab, mepolizumab, tocilizumab, ustekinumab, ibritumomab tiuxetan, tositumomab, abagovomab, adecatumumab, alemtuzumab, anti-CD30 monoclonal antibody Xmab2513, anti-MET monoclonal antibody MetMab, apolizumab, apomab, arcitumomab, basiliximab, bispecific antibody 2B1, blinatumomab, brentuximab vedotin, capromab pendetide, cixutumumab, claudiximab, conatumumab, dacetuzumab, denosumab, eculizumab, epratuzumab, ertumaxomab, etaracizumab, figitumumab, fresolimumab, galiximab, ganitumab, gemtuzumab ozogamicin, glembatumumab, ibritumomab, inotuzumab ozogamicin, ipilimumab, lexatumumab, lintuzumab, lintuzumab, lucatumumab, mapatumumab, matuzumab, milatuzumab, monoclonal antibody CC49, necitumumab, nimotuzumab, ofatumumab, oregovomab, pertuzumab, ramacurimab, ranibizumab, siplizumab, sonepcizumab, tanezumab, tositumomab, trastuzumab, tremelimumab, tucotuzumab celmoleukin, veltuzumab, visilizumab, volociximab, and zalutumumab.

In the context of combination therapy, administration of the apilimod composition may be simultaneous with or sequential to the administration of the one or more additional active agents. In another embodiment, administration of the different components of a combination therapy may be at different frequencies. The one or more additional agents may be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a compound of the present invention.

The one or more additional active agents can be formulated for co-administration with an apilimod composition in a single dosage form, as described in greater detail herein. The one or more additional active agents can be administered separately from the dosage form that comprises the compound of the present invention. When the additional active agent is administered separately from the apilimod composition, it can be by the same or a different route of administration as the apilimod composition.

Preferably, the administration of an apilimod composition in combination with one or more additional agents provides a synergistic response in the subject being treated. In this context, the term "synergistic" refers to the efficacy of the combination being more effective than the additive effects of either single therapy alone. The synergistic effect of a combination therapy according to the invention can permit the use of lower dosages and/or less frequent administration of at least one agent in the combination compared to its dose and/or frequency outside of the combination. Additional beneficial effects of the combination can be manifested in the avoidance or reduction of adverse or unwanted side effects associated with the use of either therapy in the combination alone (also referred to as monotherapy).

"Combination therapy" also embraces the administration of the compounds of the present invention in further combination with non-drug therapies (e.g., surgery or radiation treatment). Where the combination therapy further comprises a non-drug treatment, the non-drug treatment may be conducted at any suitable time so long as a beneficial effect from the co-action of the combination of the therapeutic compounds and non-drug treatment is achieved. For example, in appropriate cases, the beneficial effect is still achieved when the non-drug treatment is temporally removed from the administration of the therapeutic compounds, perhaps by days or even weeks.

The non-drug treatment can be selected from chemotherapy, radiation therapy, hormonal therapy, anti-estrogen therapy, gene therapy, and surgery. For example, a non-drug therapy is the removal of an ovary (e.g., to reduce the level of estrogen in the body), thoracentesis (e.g., to remove fluid from the chest), paracentesis (e.g., to remove fluid from the abdomen), surgery to remove or shrink angiomyolipomas, lung transplantation (and optionally with an antibiotic to prevent infection due to transplantation), or oxygen therapy (e.g., through a nasal cannula containing two small plastic tubes or prongs that are placed in both nostrils, through a face mask that fits over the nose and mouth, or through a small tube inserted into the windpipe through the front of the neck, also called transtracheal oxygen therapy).

The present invention also provides methods of treating mTOR-related diseases, disorders, and conditions, in a subject in need thereof by administering to the subject a therapeutically effective amount of an apilimod composition of the invention. Such diseases and disorders include, for example, cancers in which mTOR is dysregulated. mTOR dysregulation has been implicated in 70% of all cancers. See e.g., Menon et al *Oncogene* 27 (2009):S43-S51. Specific cancers having a component of mTOR dysregulation include brain tumors such as gliomas (e.g., glioblastoma multiforme), sarcoma, breast cancer, lung cancer (e.g., non-small-cell lung cancer), mesothelioma, appendiceal cancer, genitourinary cancers (e.g., renal cell carcinoma, prostate, bladder, testicular, penile, cervical cancer, ovarian cancer, von Hippel Lindau disease), head and neck cancer, gastrointestinal tumors (e.g., hepatocellular carcinoma, gallbladder cancer, esophageal cancer, gastric cancer, colorectal cancer, or pancreatic cancer), neuroendocrine tumors (NETs), thyroid tumor, pituitary tumor, adrenal tumor, hematological malignancy (e.g., Non-Hodgkin's lymphoma, mantle cell lymphoma, myeloma, B-cell lymphoma, leukemia, Hodgkin's lymphoma), or metastatic forms of one or more of the cancers described herein. See e.g., Laplante et al. *Cell* 149 (2012):274-293.

In the context of the methods described herein, the amount of an apilimod composition administered to the subject is a therapeutically effective amount. The term "therapeutically effective amount" refers to an amount sufficient to treat, ameliorate a symptom of, reduce the severity of, or reduce the duration of the disease or disorder being treated, or enhance or improve the therapeutic effect of another therapy, or sufficient to exhibit a detectable therapeutic effect in the subject. In one embodiment, the therapeutically effective amount of an apilimod composition is the amount effective to inhibit PIKfyve kinase activity.

An effective amount of an apilimod composition can range from about 0.001 mg/kg to about 1000 mg/kg, about 0.01 mg/kg to about 100 mg/kg, about 10 mg/kg to about 250 mg/kg, about 0.1 mg/kg to about 15 mg/kg; or any range in which the low end of the range is any amount between 0.001 mg/kg and 900 mg/kg and the upper end of the range is any amount between 0.1 mg/kg and 1000 mg/kg (e.g., 0.005 mg/kg and 200 mg/kg, 0.5 mg/kg and 20 mg/kg). Effective doses will also vary, as recognized by those skilled in the art, depending on the diseases treated, route of administration, excipient usage, and the possibility of co-usage with other therapeutic treatments such as use of other agents. See, e.g., U.S. Pat. No. 7,863,270, incorporated herein by reference.

In more specific aspects, an apilimod composition is administered at a dosage regimen of 30-1000 mg/day (e.g., 30, 35, 40, 45, 50, 55, 60, 65, 70, 75, 80, 85, 90, 95, 100, 125, 150, 175, 200, 225, 250, 275, or 300 mg/day) for at least 1 week (e.g., 1, 2, 3, 4, 5, 6, 7, 8, 9, 10, 11, 12, 36, 48, or more weeks). Preferably, an apilimod composition is administered at a dosage regimen of 100-1000 mg/day for 4 or 16 weeks. Alternatively or subsequently, an apilimod composition is administered at a dosage regimen of 100 mg-300 mg twice a day for 8 weeks, or optionally, for 52 weeks. Alternatively or subsequently, an apilimod composition is administered at a dosage regimen of 50 mg-1000 mg twice a day for 8 weeks, or optionally, for 52 weeks.

An effective amount of the apilimod composition can be administered once daily, from two to five times daily, up to two times or up to three times daily, or up to eight times daily. In one embodiment, the apilimod composition is administered thrice daily, twice daily, once daily, fourteen days on (four times daily, thrice daily or twice daily, or once daily) and 7 days off in a 3-week cycle, up to five or seven days on (four times daily, thrice daily or twice daily, or once daily) and 14-16 days off in 3 week cycle, or once every two days, or once a week, or once every 2 weeks, or once every 3 weeks.

In accordance with the methods described herein, a "subject in need of" is a subject having a disease, disorder or condition, or a subject having an increased risk of developing a disease, disorder or condition relative to the population at large. The subject in need thereof can be one that is "non-responsive" or "refractory" to a currently available therapy for the disease or disorder, for example cancer. In this context, the terms "non-responsive" and "refractory" refer to the subject's response to therapy as not clinically adequate to relieve one or more symptoms associated with the disease or disorder. In one aspect of the methods described here, the subject in need thereof is a subject having cancer whose cancer is refractory to standard therapy or whose cancer has recurred following standard treatment.

A "subject" includes a mammal. The mammal can be e.g., any mammal, e.g., a human, primate, vertebrate, bird, mouse, rat, fowl, dog, cat, cow, horse, goat, camel, sheep or a pig. Preferably, the mammal is a human. The term "patient" refers to a human subject.

The present invention also provides a monotherapy for the treatment of a disease, disorder or condition as described herein. As used herein, "monotherapy" refers to the administration of a single active or therapeutic compound to a subject in need thereof.

As used herein, "treatment", "treating" or "treat" describes the management and care of a patient for the purpose of combating a disease, condition, or disorder and includes the administration of an apilimod composition to alleviate the symptoms or complications of a disease, condition or disorder, or to eliminate the disease, condition or disorder.

As used herein, "prevention", "preventing" or "prevent" describes reducing or eliminating the onset of the symptoms or complications of the disease, condition or disorder and includes the administration of an apilimod composition to reduce the onset, development or recurrence of symptoms of the disease, condition or disorder.

In one embodiment, the administration of an apilimod composition leads to the elimination of a symptom or complication of the disease or disorder being treated, however, elimination is not required. In one embodiment, the severity of the symptom is decreased. In the context of cancer, such symptoms may include clinical markers of severity or progression including the degree to which a tumor secrets growth factors, degrades the extracellular matrix, becomes vascularized, loses adhesion to juxtaposed tissues, or metastasizes, as well as the number of metastases.

Treating cancer according to the methods described herein can result in a reduction in size of a tumor. A reduction in size of a tumor may also be referred to as "tumor regression". Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating cancer according to the methods described herein can result in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

Treating cancer according to the methods described herein can result in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating cancer according to the methods described herein can result in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

Treating a disorder, disease or condition according to the methods described herein can result in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating a disorder, disease or condition according to the methods described herein can result in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating a disorder, disease or condition according to the methods described herein can result in increase in average survival time of a population of treated subjects in comparison to a population receiving monotherapy with a drug that is not an apilimod composition as described herein. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating a disorder, disease or condition according to the methods described herein can result in a decrease in the mortality rate of a population of treated subjects in comparison to a population receiving carrier alone. Treating a disorder, disease or condition according to the methods described herein can result in a decrease in the mortality rate of a population of treated subjects in comparison to an untreated population. Treating a disorder, disease or condition according to the methods described herein can result in a decrease in the mortality rate of a population of treated subjects in comparison to a population receiving monotherapy with a drug that is not an apilimod composition. Preferably, the mortality rate is decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

Treating a disorder, disease or condition according to the methods described herein can result in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate can be measured according to a change in tumor diameter per unit time. In one embodiment, after treatment the tumor growth rate may be about zero and is determined to maintain the same size, e.g., has stopped growing.

Treating a disorder, disease or condition according to the methods described herein can result in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating or preventing a cell proliferative disorder according to the methods described herein can result in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. The rate of cellular proliferation is measured, for example, by measuring the number of dividing cells in a tissue sample per unit time.

Treating or preventing a cell proliferative disorder according to the methods described herein can result in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. Preferably, the proportion of proliferating cells is measured, for example, by quantifying the number of dividing cells relative to the number of nondividing cells in a tissue sample. The proportion of proliferating cells can be equivalent to the mitotic index.

Treating or preventing a cell proliferative disorder according to the methods described herein can result in a decrease in the size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. The size of an area or zone of cellular proliferation may be measured by any reproducible means of measurement. The size of an area or zone of cellular proliferation may be measured as a diameter or width of an area or zone of cellular proliferation.

Treating or preventing a cell proliferative disorder according to the methods described herein can result in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. An abnormal cellular morphology can be measured by microscopy, e.g., using an inverted tissue culture microscope. An abnormal cellular morphology can take the form of nuclear pleiomorphism.

As used herein, the term "selectively" means tending to occur at a higher frequency in one population than in another population. The compared populations can be cell populations. Preferably, an apilimod composition as described herein acts selectively on hyper-proliferating cells or abnormally proliferating cells, compared to normal cells. As used herein, a "normal cell" is a cell that cannot be classified as part of a "cell proliferative disorder". A normal cell lacks unregulated or abnormal growth, or both, that can lead to the development of an unwanted condition or disease. Preferably, a normal cell possesses normally functioning cell cycle checkpoint control mechanisms. Preferably, an apilimod composition acts selectively to modulate one molecular target (e.g., a target kinase) but does not significantly modulate another molecular target (e.g., a non-target kinase). The invention also provides a method for selectively inhibiting the activity of an enzyme, such as a kinase. Preferably, an event occurs selectively in population A relative to population B if it occurs greater than two times more frequently in population A as compared to population B. An event occurs selectively if it occurs greater than five times more frequently in population A. An event occurs selectively if it occurs greater than ten times more frequently in population A; more preferably, greater than fifty times; even more preferably, greater than 100 times; and most preferably, greater than 1000 times more frequently in population A as compared to population B. For example, cell death would be said to occur selectively in diseased or hyper-proliferating cells if it occurred greater than twice as frequently in diseased or hyper-proliferating cells as compared to normal cells.

Pharmaceutical Compositions and Formulations

The present invention provides apilimod compositions that are preferably pharmaceutically acceptable compositions suitable for use in a mammal, preferably a human. In this context, the compositions may further comprise at least one pharmaceutically acceptable excipient or carrier, wherein the amount is effective for the treatment of a disease or disorder. In one embodiment, the disease or disorder is cancer, preferably a lymphoma, and most preferably a B cell lymphoma. In one embodiment, the disease or disorder is an mTOR disease or disorder.

In one embodiment, the apilimod composition comprises apilimod free base or apilimod dimesylate.

In one embodiment, the apilimod composition is combined with at least one additional active agent in a single dosage form. In one embodiment, the composition further comprises an antioxidant.

In one embodiment, the at least one additional active agent is selected from the group consisting of an alkylating agent, an intercalating agent, a tublin binding agent, a corticosteroid, and combinations thereof. In one embodiment, the at least one additional active agent is a therapeutic agent selected from the group consisting of ibrutinib, rituximab, doxorubicin, prednisolone, vincristine, velcade, and everolimus, and combinations thereof. In one embodiment, the at least one additional active agent is a therapeutic agent selected from cyclophosphamide, hydroxydaunorubicin (also referred to as doxorubicin or Adriamycin™) vincristine (also referred to as Oncovin™), prednisone, prednisolone, and combinations thereof. In one embodiment, the at least one additional active agent is a non-therapeutic agent selected to ameliorate one or more side effects of the apilimod composition. In one embodiment, the non-therapeutic agent is selected from the group consisting of ondansetron, granisetron, dolasetron and palonosetron. In one embodiment, the non-therapeutic agent is selected from the group consisting of pindolol and risperidone.

In one embodiment, the at least one additional active agent is selected from an inhibitor of the mTOR pathway, a PI3K inhibitor, a dual PI3K/mTOR inhibitor, a SRC inhibitor, a VEGF inhibitor, a Janus kinase (JAK) inhibitor, a Raf inhibitor, an Erk inhibitor, a farnesyltransferase inhibitor, a histone deacetylase inhibitor, an anti-mitotic agent, a multi-drug resistance efflux inhibitor, an antibiotic, and a therapeutic antibody. In one embodiment, the at least one additional active agent is selected from a farnesyltransferase inhibitor (e.g., tipifarnib), an anti-mitotic agent (e.g., docetaxel), a histone deacetylase inhibitor (e.g., vorinostat), and a multi-drug resistance efflux inhibitor.

In one embodiment, the mTOR inhibitor is selected from the group consisting of rapamycin (also referred to as sirolimus), everolimus, temsirolimus, ridaforolimus, umirolimus, zotarolimus, AZD8055, INK128, WYE-132, Torin-1, pyrazolopyrimidine analogs PP242, PP30, PP487, PP121, KU0063794, KU-BMCL-200908069-1, Wyeth-BMCL-200910075-9b, INK-128, XL388, AZD8055, P2281, and P529. See, e.g., Liu et al. Drug Disc. Today Ther. Strateg., 6(2): 47-55 (2009).

In one embodiment, the mTOR inhibitor is trans-4-[4-amino-5-(7-methoxy-1H-indol-2-yl)imidazo[5,1-f][1,2,4] triazin-7-yl]cyclohexane carboxylic acid (also known as OSI-027), and any salts, solvates, hydrates, and other physical forms, crystalline or amorphous, thereof. See US 2007/0112005. OSI-027 can be prepared according to US 2007/0112005, incorporated herein by reference. In one embodiment, the mTOR inhibitor is OXA-01. See e.g., WO 2013152342 A1.

In one embodiment, the PI3K inhibitor is selected from the group consisting of GS-1101 (Idelalisib), GDC0941 (Pictilisib), LY294002, BKM120 (Buparlisib), PI-103, TGX-221, IC-87114, XL 147, ZSTK474, BYL719, AS-605240, PIK-75, 3-methyladenine, A66, PIK-93, PIK-90, AZD6482, IPI-145 (Duvelisib), TG100-115, AS-252424, PIK294, AS-604850, GSK2636771, BAY 80-6946 (Copanlisib), CH5132799, CAY10505, PIK-293, TG100713, CZC24832 and HS-173.

In one embodiment, the dual PI3K/mTOR inhibitor is selected from the group consisting of, GDC-094, WAY-001, WYE-354, WAY-600, WYE-687, Wyeth-BMCL-200910075-16b, Wyeth-BMCL-200910096-27, KU0063794 and KUBMCL-200908069-5, NVP-BEZ235, XL-765, PF-04691502, GDC-0980 (Apitolisib), GSK1059615, PF-05212384, BGT226, PKI-402, VS-558 and GSK2126458. See, e.g., Liu et al. Drug Disc. Today Ther. Strateg., 6(2): 47-55 (2009), incorporated herein by reference.

In one embodiment, the mTOR pathway inhibitor is a polypeptide (e.g., an antibody or fragment thereof) or a nucleic acid (e.g., a double-stranded small interfering RNA, a short hairpin RNA, a micro-RNA, an antisense oligonucleotide, a locked nucleic acid, or an aptamer) that binds to and inhibits the expression level or activity or a protein (or nucleic acid encoding the protein) in the mTOR pathway. For example, the polypeptide or nucleic acid inhibits mTOR Complex 1 (mTORC1), regulatory-associated protein of mTOR (Raptor), mammalian lethal with SEC13 protein 8 (MLST8), proline-rich Akt substrate of 40 kDa (PRAS40), DEP domain-containing mTOR-interacting protein (DEPTOR), mTOR Complex 2 (mTORC2), rapamycin-insensitive companion of mTOR (RICTOR), G protein beta subunit-like (GβL), mammalian stress-activated protein kinase interacting protein 1 (mSIN1), paxillin, RhoA, Ras-related C3 botulinum toxin substrate 1 (Rac1), Cell division control protein 42 homolog (Cdc42), protein kinase C α (PKCα), the serine/threonine protein kinase Akt, phosphoinositide 3-kinase (PI3K), p70S6K, Ras, and/or eukaryotic translation initiation factor 4E (eIF4E)-binding proteins (4EBPs), or the nucleic acid encoding one of these proteins.

In one embodiment, the SRC inhibitor is selected from the group consisting of bosutinib, saracatinib, dasatinib, ponatinib, KX2-391, XL-228, TG100435/TG100855, and DCC2036. See, e.g., Puls et al. *Oncologist.* 2011 May; 16(5): 566-578. In one embodiment, the SRC inhibitor is a polypeptide (e.g., an antibody or fragment thereof) or nucleic acid (e.g., a double-stranded small interfering RNA, a short hairpin RNA, a micro-RNA, an antisense oligonucleotide, a locked nucleic acid, or an aptamer) that binds to and inhibits the expression level or activity of the SRC protein or a nucleic acid encoding the SRC protein.

In one embodiment, the VEGF inhibitor is selected from bevacizumab, sunitinib, pazopanib, axitinib, sorafenib, regorafenib, lenvatinib, and motesanib. In one embodiment, the VEGF inhibitor is a polypeptide (e.g., an antibody or fragment thereof) or nucleic acid (e.g., a double-stranded small interfering RNA, a short hairpin RNA, a micro-RNA, an antisense oligonucleotide, a morpholino, a locked nucleic acid, or an aptamer) that binds to and inhibits the expression level or activity of a VEGF protein, a VEGF receptor protein, or a nucleic acid encoding one of these proteins. For example, the VEGF inhibitor is a soluble VEGF receptor (e.g., a soluble VEGF-C/D receptor (sVEGFR-3)).

In one embodiment, the JAK inhibitor is selected from facitinib, ruxolitinib, baricitinib, CYT387 (CAS number 1056634-68-4), lestaurtinib, pacritinib, and TG101348 (CAS number 936091-26-8). In one embodiment, the JAK inhibitor is a polypeptide (e.g., an antibody or fragment thereof) or nucleic acid (e.g., a double-stranded small interfering RNA, a short hairpin RNA, a micro-RNA, an antisense oligonucleotide, a morpholino, a locked nucleic acid, or an aptamer) that binds to and inhibits the expression level or activity of a JAK (e.g., JAK1, JAK2, JAK3, or TYK2) or a nucleic acid encoding the JAK protein.

In one embodiment, the Raf inhibitor is selected from PLX4032 (vemurafenib), sorafenib, PLX-4720, GSK2118436 (dabrafenib), GDC-0879, RAF265, AZ 628, NVP-BHG712, SB90885, ZM 336372, GW5074, TAK-632, CEP-32496 and LGX818 (Encorafenib). In one embodiment, the Raf inhibitor is a polypeptide (e.g., an antibody or fragment thereof) or nucleic acid (e.g., a double-stranded small interfering RNA, a short hairpin RNA, a micro-RNA, an antisense oligonucleotide, a morpholino, a locked nucleic acid, or an aptamer) that binds to and inhibits the expression level or activity of a Raf (e.g., A-Raf, B-Raf, C-Raf) or a nucleic acid encoding the Raf protein. In one embodiment, the MEK inhibitor is selected from AZD6244 (Selumetinib), PD0325901, GSK1120212 (Trametinib), U0126-EtOH, PD184352, RDEA119 (Rafametinib), PD98059, BIX 02189, MEK162 (Binimetinib), AS-703026 (Pimasertib), SL-327, BIX02188, AZD8330, TAK-733 and PD318088. In one embodiment, the MEK inhibitor is a polypeptide (e.g., an antibody or fragment thereof) or nucleic acid (e.g., a double-stranded small interfering RNA, a short hairpin RNA, a micro-RNA, an antisense oligonucleotide, a morpholino, a locked nucleic acid, or an aptamer) that binds to and inhibits the expression level or activity of a MEK (e.g., MEK-1, MEK-2) or a nucleic acid encoding the MEK protein.

In one embodiment, the Akt inhibitor is selected from MK-2206, KRX-0401 (perifosine), GSK690693, GDC-0068 (Ipatasertib), AZD5363, CCT128930, A-674563, PHT-427. In one embodiment, the Akt inhibitor is a polypeptide (e.g., an antibody or fragment thereof) or nucleic acid (e.g., a double-stranded small interfering RNA, a short hairpin RNA, a micro-RNA, an antisense oligonucleotide, a morpholino, a locked nucleic acid, or an aptamer) that binds to and inhibits the expression level or activity of a Akt (e.g., Akt-1, Akt-2, Akt-3) or a nucleic acid encoding the Akt protein.

In one embodiment, the farnesyltransferase inhibitor is selected from LB42708 or tipifarnib. In one embodiment, the farnesyltransferase inhibitor is a polypeptide (e.g., an antibody or fragment thereof) or nucleic acid (e.g., a double-stranded small interfering RNA, a short hairpin RNA, a micro-RNA, an antisense oligonucleotide, a morpholino, a locked nucleic acid, or an aptamer) that binds to and inhibits the expression level or activity of farnesyltransferase or a nucleic acid encoding the farnesyltransferase protein. In one embodiment, the histone modulating inhibitor is selected from anacardic acid, C646, MG149 (histone acetyltransferase), GSK J4 Hcl (histone demethylase), GSK343 (active against EZH2), BIX 01294 (histone methyltransferase), MK0683 (Vorinostat), MS275 (Entinostat), LBH589 (Panobinostat), Trichostatin A, MGCD0103 (Mocetinostat), Tasquinimod, TMP269, Nexturastat A, RG2833, PDX101 (Belinostat).

In one embodiment, the anti-mitotic agent is selected from Griseofulvin, vinorelbine tartrate, paclitaxel, docetaxel, vincristine, vinblastine, Epothilone A, Epothilone B, ABT-751, CYT997 (Lexibulin), vinflunine tartrate, Fosbretabulin, GSK461364, ON-01910 (Rigosertib), Ro3280, BI2536, NMS-P937, BI 6727 (Volasertib), HMN-214 and MLN0905.

In one embodiment, the polyether antibiotic is selected from sodium monensin, nigericin, valinomycin, salinomycin.

A "pharmaceutical composition" is a formulation containing the compounds described herein in a pharmaceutically acceptable form suitable for administration to a subject. As used herein, the phrase "pharmaceutically acceptable" refers to those compounds, materials, compositions, carriers, and/ or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. Examples of pharmaceutically acceptable excipients include, without limitation, sterile liquids, water, buffered saline, ethanol, polyol (for example, glycerol, propylene glycol, liquid polyethylene glycol and the like), oils, detergents, suspending agents, carbohydrates (e.g., glucose, lactose, sucrose or dextran), antioxidants (e.g., ascorbic acid or glutathione), chelating agents, low molecular weight proteins, or suitable mixtures thereof.

A pharmaceutical composition can be provided in bulk or in dosage unit form. It is especially advantageous to formulate pharmaceutical compositions in dosage unit form for ease of administration and uniformity of dosage. The term "dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved. A dosage unit form can be an ampoule, a vial, a suppository, a dragee, a tablet, a capsule, an IV bag, or a single pump on an aerosol inhaler.

In therapeutic applications, the dosages vary depending on the agent, the age, weight, and clinical condition of the recipient patient, and the experience and judgment of the clinician or practitioner administering the therapy, among other factors affecting the selected dosage. Generally, the dose should be a therapeutically effective amount. Dosages can be provided in mg/kg/day units of measurement (which dose may be adjusted for the patient's weight in kg, body surface area in $m^2$, and age in years). An effective amount of a pharmaceutical composition is that which provides an objectively identifiable improvement as noted by the clinician or other qualified observer. For example, alleviating a symptom of a disorder, disease or condition. As used herein, the term "dosage effective manner" refers to amount of a pharmaceutical composition to produce the desired biological effect in a subject or cell.

For example, the dosage unit form can comprise 1 nanogram to 2 milligrams, or 0.1 milligrams to 2 grams; or from 10 milligrams to 1 gram, or from 50 milligrams to 500 milligrams or from 1 microgram to 20 milligrams; or from 1 microgram to 10 milligrams; or from 0.1 milligrams to 2 milligrams.

The pharmaceutical compositions can take any suitable form (e.g., liquids, aerosols, solutions, inhalants, mists, sprays; or solids, powders, ointments, pastes, creams, lotions, gels, patches and the like) for administration by any desired route (e.g., pulmonary, inhalation, intranasal, oral, buccal, sublingual, parenteral, subcutaneous, intravenous, intramuscular, intraperitoneal, intrapleural, intrathecal, transdermal, transmucosal, rectal, and the like). For example, a pharmaceutical composition of the invention may be in the form of an aqueous solution or powder for aerosol administration by inhalation or insufflation (either through the mouth or the nose), in the form of a tablet or capsule for oral administration; in the form of a sterile aqueous solution or dispersion suitable for administration by either direct injection or by addition to sterile infusion fluids for intravenous infusion; or in the form of a lotion, cream, foam, patch, suspension, solution, or suppository for transdermal or transmucosal administration.

A pharmaceutical composition can be in the form of an orally acceptable dosage form including, but not limited to, capsules, tablets, buccal forms, troches, lozenges, and oral liquids in the form of emulsions, aqueous suspensions, dispersions or solutions. Capsules may contain mixtures of a compound of the present invention with inert fillers and/or diluents such as the pharmaceutically acceptable starches (e.g., corn, potato or tapioca starch), sugars, artificial sweetening agents, powdered celluloses, such as crystalline and microcrystalline celluloses, flours, gelatins, gums, etc. In the case of tablets for oral use, carriers which are commonly used include lactose and corn starch. Lubricating agents, such as magnesium stearate, can also be added. For oral administration in a capsule form, useful diluents include lactose and dried corn starch. When aqueous suspensions and/or emulsions are administered orally, the compound of the present invention may be suspended or dissolved in an oily phase is combined with emulsifying and/or suspending agents. If desired, certain sweetening and/or flavoring and/or coloring agents may be added.

A pharmaceutical composition can be in the form of a tablet. The tablet can comprise a unit dosage of a compound of the present invention together with an inert diluent or carrier such as a sugar or sugar alcohol, for example lactose, sucrose, sorbitol or mannitol. The tablet can further comprise a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. The tablet can further comprise binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures.

The tablet can be a coated tablet. The coating can be a protective film coating (e.g. a wax or varnish) or a coating designed to control the release of the active agent, for example a delayed release (release of the active after a predetermined lag time following ingestion) or release at a particular location in the gastrointestinal tract. The latter can be achieved, for example, using enteric film coatings such as those sold under the brand name Eudragit®.

Tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Preferred surface modifying agents include nonionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine.

A pharmaceutical composition can be in the form of a hard or soft gelatin capsule. In accordance with this formulation, the compound of the present invention may be in a solid, semi-solid, or liquid form.

A pharmaceutical composition can be in the form of a sterile aqueous solution or dispersion suitable for parenteral administration. The term parenteral as used herein includes subcutaneous, intracutaneous, intravenous, intramuscular, intra-articular, intraarterial, intrasynovial, intrasternal, intrathecal, intralesional and intracranial injection or infusion techniques.

A pharmaceutical composition can be in the form of a sterile aqueous solution or dispersion suitable for administration by either direct injection or by addition to sterile infusion fluids for intravenous infusion, and comprises a solvent or dispersion medium containing, water, ethanol, a polyol (e.g., glycerol, propylene glycol and liquid polyethylene glycol), suitable mixtures thereof, or one or more vegetable oils. Solutions or suspensions of the compound of the present invention as a free base or pharmacologically acceptable salt can be prepared in water suitably mixed with a surfactant. Examples of suitable surfactants are given below. Dispersions can also be prepared, for example, in glycerol, liquid polyethylene glycols and mixtures of the same in oils.

The pharmaceutical compositions for use in the methods of the present invention can further comprise one or more additives in addition to any carrier or diluent (such as lactose or mannitol) that is present in the formulation. The one or more additives can comprise or consist of one or more surfactants. Surfactants typically have one or more long aliphatic chains such as fatty acids which enables them to insert directly into the lipid structures of cells to enhance drug penetration and absorption. An empirical parameter commonly used to characterize the relative hydrophilicity and hydrophobicity of surfactants is the hydrophilic-lipophilic balance ("HLB" value). Surfactants with lower HLB values are more hydrophobic, and have greater solubility in oils, while surfactants with higher HLB values are more hydrophilic, and have greater solubility in aqueous solutions. Thus, hydrophilic surfactants are generally considered to be those compounds having an HLB value greater than about 10, and hydrophobic surfactants are generally those having an HLB value less than about 10. However, these HLB values are merely a guide since for many surfactants, the HLB values can differ by as much as about 8 HLB units, depending upon the empirical method chosen to determine the HLB value.

Among the surfactants for use in the compositions of the invention are polyethylene glycol (PEG)-fatty acids and PEG-fatty acid mono and diesters, PEG glycerol esters, alcohol-oil transesterification products, polyglyceryl fatty acids, propylene glycol fatty acid esters, sterol and sterol derivatives, polyethylene glycol sorbitan fatty acid esters, polyethylene glycol alkyl ethers, sugar and its derivatives, polyethylene glycol alkyl phenols, polyoxyethylene-polyoxypropylene (POE-POP) block copolymers, sorbitan fatty acid esters, ionic surfactants, fat-soluble vitamins and their salts, water-soluble vitamins and their amphiphilic derivatives, amino acids and their salts, and organic acids and their esters and anhydrides.

The present invention also provides packaging and kits comprising pharmaceutical compositions for use in the methods of the present invention. The kit can comprise one or more containers selected from the group consisting of a bottle, a vial, an ampoule, a blister pack, and a syringe. The kit can further include one or more of instructions for use in treating and/or preventing a disease, condition or disorder of the present invention, one or more syringes, one or more applicators, or a sterile solution suitable for reconstituting a pharmaceutical composition of the present invention.

All percentages and ratios used herein, unless otherwise indicated, are by weight. Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

EXAMPLES

Example 1: Apilimod is a Highly Selective Inhibitor of TSC2 Null Cell Proliferation Apilimod was identified in a high throughput cell viability screen using TSC2-/- mouse embryonic fibroblasts (MEF-EV) cells. TSC2 null cells have constitutively active mTOR. Briefly, MEF cells derived from TSC2-/- knockout mouse embryos (Onda et al., *J. Clin. Invest.* 104(6):687-95, 1999) were infected with a retrovirus vector encoding the hygromycin antibiotic resistance gene (MEF-EV) or the same retrovirus vector also encoding TSC2 (MEF-TSC2). The MEF-EV and MEF-TSC2 line were then established by hygromycin selection.

Cells were expanded in DMEM containing 10% FBS (Omega Scientific) and 2 mM L-Glutamine. Frozen stocks of cells were prepared for direct use in the HTS assay. Cells were harvested, pelleted and then resuspended in 95% FBS & 5% DMSO at a concentration $1 \times 10^7$ cells/ml. One ml aliquots were rate frozen to −80 at a rate of 1 degree per minute. These stocks were then transferred to vapor phase liquid nitrogen for long term storage.

For screening, vials were thawed at 37° C. with continuous agitation until just thawed then re-suspended in room temperature assay media and centrifuged at 1,000 rpm for 5 minutes. The resulting pellet was re-suspended in appropriate volume and counted using an automated cell counter and diluted accordingly to a final count of 40,000 cells/ml. Test compounds (5 μl stock solution, 6× desired final well concentration) were dispensed to 384-well assay plates (Corning 3712) using a Biomek FX liquid handler. MEF-EV cells (1000 cells per well in 25 μL of media) were added to these pre-formatted plates using a Thermo Wellmate, non-contact dispensing system with a standard bore cassette head. Plates were incubated for 72 h at 37° C. under an atmosphere of 5% $CO_2$ in a humidified incubator.

Cell viability was determined with CellTiter-Glo® luminescence assay (Promega) as per the manufacturer's instructions. Viability was expressed as a percentage of untreated control cells. As an example, for apilimod, MEF-EV cell viability (Mean+/−StDev, n=3) was 2.16+/−0.36%@0.5 μM and 1.94+/−0.07%@5 μM.

The activity of apilimod on TSC2 deficient cells was further demonstrated by performing 10 point dose response on the MEF-EV and MEF-TSC2 lines described above as well as three additional pairs of isogenic lines: (1) (TSC2-/-, p53-/-) and (TSC2+/-, p53-/-) MEF lines were established from (TSC2-/-, p53-/-) or (TSC2+/-, p53-/-) embryos according to standard methods. See e.g., Zhang et al. *J. Clin. Invest.* 112, 1223-33, 2003. (2) ELT3-EV and ELT3-TSC2 lines were established from the ELT3 rat tumor cell line. The ELT3 line is an established rat tumor model for LAM/TSC. See e.g., Howe et al., *Am. J. Path.* 146, 1568-79, 1995. These cells harbor an inactivating mutation in TSC2, which leads to constitutive activation of the mTOR pathway. To develop an isogenic pair of cells ELT3 cells were infected with a retrovirus vector encoding the hygromycin antibiotic resistance gene (ELT3-EV) or the same retrovirus vector also encoding TSC2 (ELT3-TSC2). The ELT3-EV and ELT3-TSC2 line were then established by hygromycin selection. (3) TRI-AML102 and AML103 lines were established from a TSC2 null primary human AML sample provided by Dr. Elizabeth Henske (Fox Chase Cancer Center, Philadelphia, Pa.). The cells were infected with amphotropic retrovirus LXSN16E6E7 that encodes the HPV16 E6 and E7 open reading frames and neomycin resistance cassette. Cells were expanded and neomycin-selected. Individual clones were isolated and frozen down. The coding sequence for the human Telomerase gene (hTERT) with hygromycin resistance cassette (pLXSN hTERT-hyg plasmid) was stably expressed into a TSC2$^{-/-}$ confirmed E6E7 AML clone using Fugene6 transfection reagent (Roche Applied Science, Indianapolis, Ind.). TRI-AML102 was generated by stable incorporation of a control zeomycin selection plasmid (pcDNA3.1-zeo), while TRI-AML103 expresses the human TSC2 cDNA pcDNA3.1-zeo plasmid. As a result of these engineering processes, both TRI102 and TRI103 are neomycin, hygromycin, and zeomycin resistant lines.

For 10-point dose response, 750 MEF, 2000 ELT3, or 2000 AML cells in 100 μL of growth media (DMEM (CellGro 10-017-CV) FBS 10% (Sigma Aldrich F2442-500ML, Lot 12D370) Penicillin/Streptomycin (100×) (CellGro Ref 30-002) were plated per well of a 96 well plate. 24 hours after plating cells, the media was removed and apilimod dilutions (1-500 nM, 2-fold dilutions) in 100 μL of growth media were added (0.1% final DMSO concentration). 72 hours after compound addition, relative cell viability was determined by CellTiter-Glo® luminescence assay (Promega) and expressed as a percentage relative to vehicle (DMSO) treated control cells. $IC_{50}$ values were then calculated from the dose response curves using XLFIT (IDBS).

The TSC2 deficient cells were highly sensitive to apilimod ($IC_{50}$=20 nM, FIG. 1). TSC2−/− p53−/− MEFs demonstrated increased sensitivity to apilimod compared to the TSC2+/− p53−/− MEFs as indicated by a selectivity ratio above 1 (2.45).

TABLE 1

$IC_{50}$ (viability) of apilimod in various cell types

| | Cell type: | | | |
|---|---|---|---|---|
| | MEF TSC2−/− | MEF TSC2−/− p53−/− | AML TSC2+/− p53−/− | ELT3 |
| IC50 TSC2−/− | 19.70 | 28.80 | 117.00 | 13.70 |
| IC50 TSC2 rescue | 20.10 | 70.70 | 132.00 | 16.05 |
| Selectivity Ratio | 1.02 | 2.45 | 1.13 | 1.17 |

IC50s (nM) calculated from 10-point dose response on TSC2−/− deficient and rescue lines.
IC50s are calculated from the average of two experiments.
The selectivity ratio is calculated by dividing the IC50 of the TSC2 rescue line by the TSC2−/− line.

Furthermore, higher concentrations of apilimod had higher potency on the TSC2−/− MEF-EV cells compared to the TSC2 rescue MEF-TSC2 cells. This data, coupled with the fact that apilimod is not cytotoxic on peripheral blood mononuclear cells (Wada et al., *Blood* 109, 1156-64, 2007), nor on a variety of other cancer lines including U937, HELA, Jurkat, and THP-1 (PCT Publication No. WO 2006/128129) suggests that there will be a high therapeutic index for treating TSC2−/− cancer cells with apilimod (FIG. 2A-2C).

Example 2: Apilimod is a Highly Selective Cytotoxic Agent in Cancer Cells

The cytotoxic activity of apilimod was evaluated using a standard cell viability assay such as CellTiterGlo™ according to the manufacturer's instructions. 122 human cancer cell lines were evaluated for sensitivity to apilimod. A cell line was called as apilimod sensitive if the $IC_{50}$ was less than 500 nM. 35 cell lines were identified as sensitive to apilimod-induced cytotoxicity. Apilimod was also highly selective for cancer cells compared to normal cells, which had $IC_{50}$'s ranging from 20-200 fold higher than the cancer cells (FIG. 2A-2C).

Figure 2A:
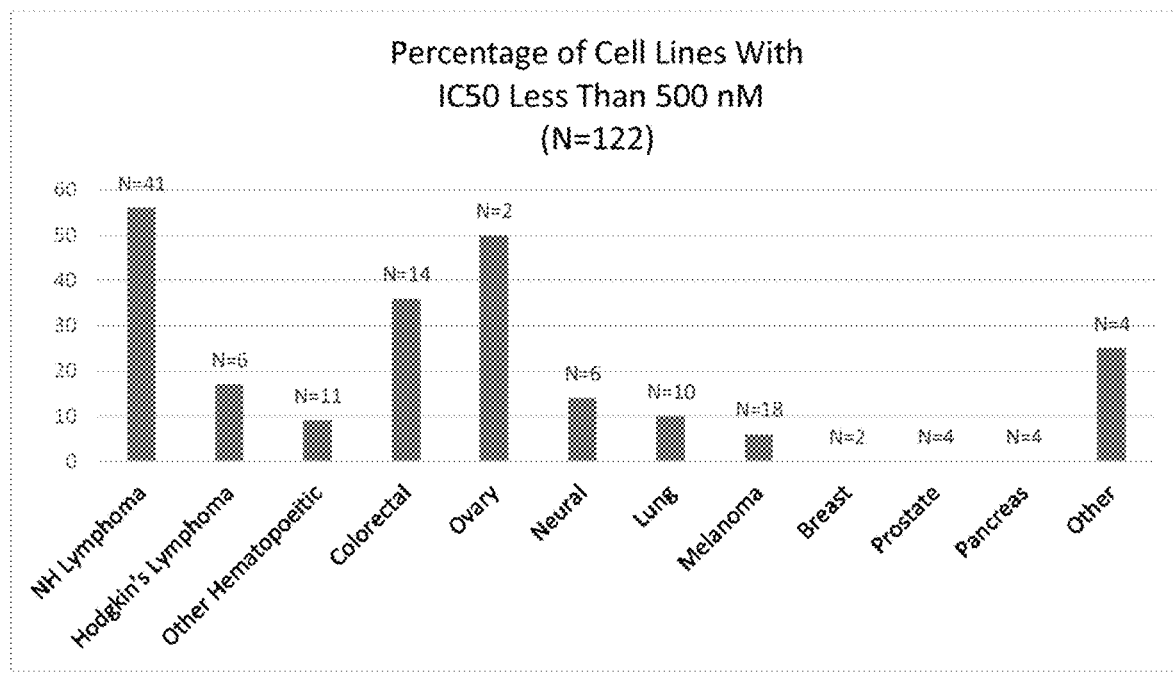
FIG. 2A: Sensitivity of cancer cell lines to apilimod (percentage of cell lines with $IC_{50}$ less than 500 nM).
Figure 2B:
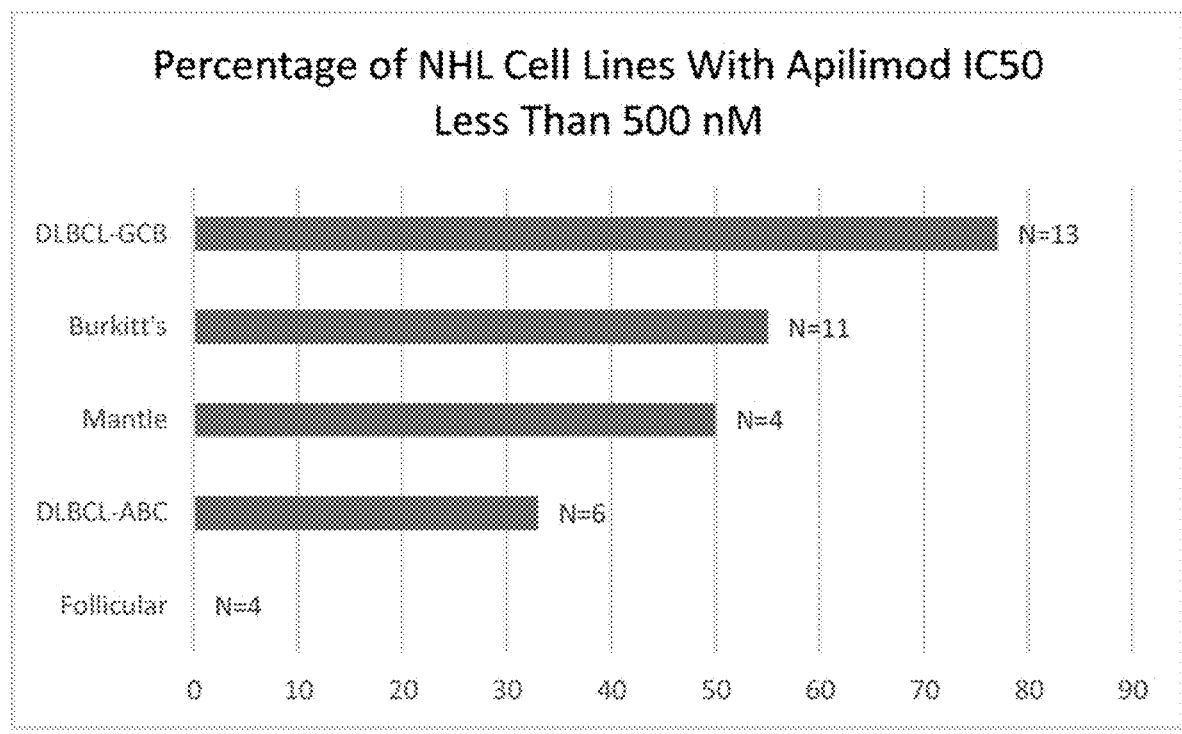
FIG. 2B: NHL cell lines are particularly sensitive to apilimod (percentage of cell lines with $IC_{50}$ less than 500 nM).
Figure 2C:
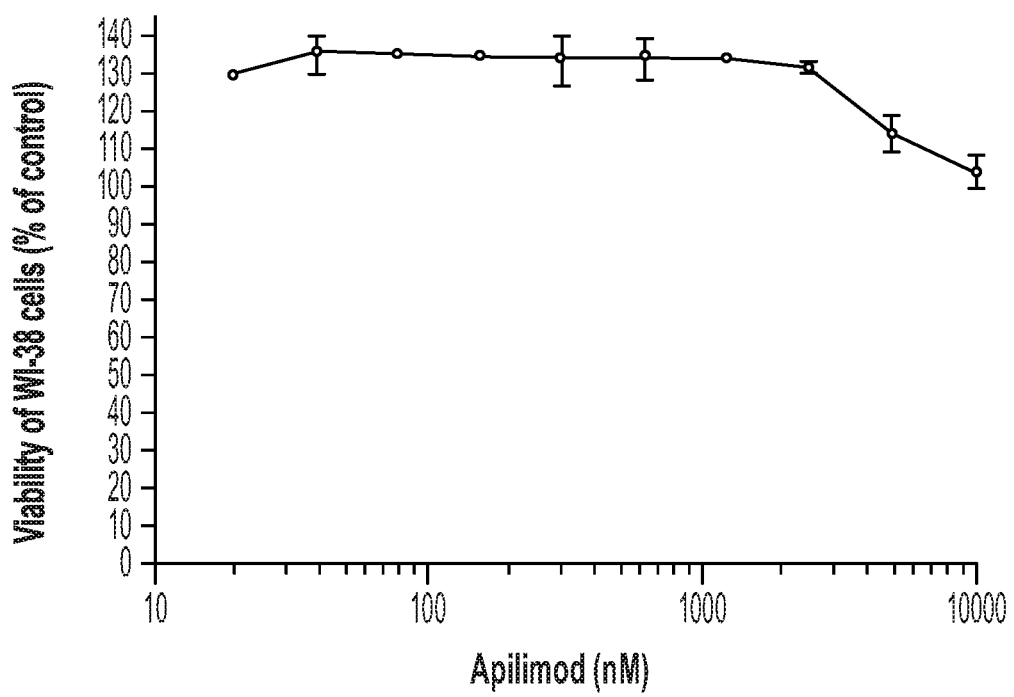
FIG. 2C: Apilimod's cytotoxic activity is selective for cancer cells over normal cells. Normal lung fibroblasts were insensitive to apilimod-induced cytotoxicity at concentrations as high as 10 micromolar.
Figure 3:
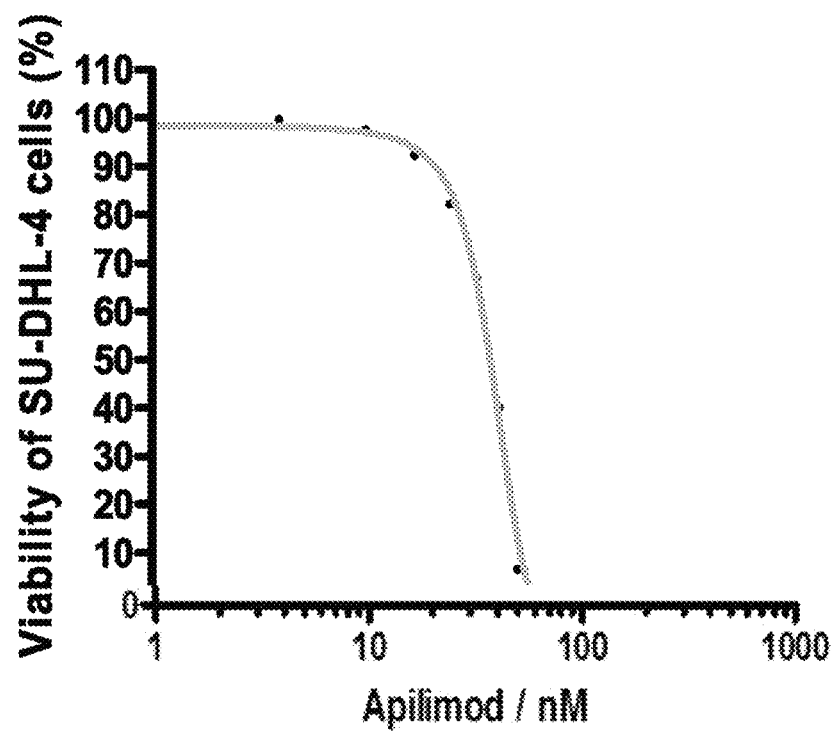
FIG. 3: a diffuse large B cell lymphoma, SUDHL-4, exhibited an $IC_{50}$ of 50 nM.

FIG. 2A shows that the apilimod-sensitive cells included cells derived from several different cancers including non-Hodgkin's lymphoma, Hodgkin's lymphoma, colorectal cancer, and lung cancer. The most sensitive of those tested were non-Hodgkin's Lymphoma (NHL) cell lines. Just over 50% of the NHL cell lines tested were sensitive to apilimod. NHL represents a diverse group of hematopoietic malignancies that vary in severity, with subtypes ranging from slow growing to aggressive. Subtypes of NHL include diffuse large B cell lymphoma (DLBCL), Burkitt's lymphoma, mantle lymphoma, and follicular B cell lymphoma. DLBCL is divided into two subtypes, GCB and ABC, based on gene expression and cell of origin. The GCB are germinal center B cell type, arising from normal germinal center B cells, and the ABC are activated B cell type, arising from post-germinal center B cells in the process of differentiating into plasma cells. In the present study, we found that certain subtypes of NHL were extremely sensitive to apilimod, with $IC_{50}$ values of less than 100 nM (compared to the cutoff for sensitive/insensitive in the screen, which was 500 nM). These included a human Burkitt's lymphoma (ST486), a human mantle cell lymphoma (JeKo-1) and a human DLBCL (SUDHL-4, $IC_{50}$=50 nM). See FIG. 2B. These results indicate that apilimod may be effective against many NHL cancers, including the more aggressive subtypes that are often refractory to standard treatments.

As detailed in Examples 6 and 7, infra, we investigated the biological mechanisms underlying apilimod's selective cytotoxicity against cancers cells and found that it is due to an inhibition of intracellular trafficking and a corresponding increase in apoptosis in those cells.

Example 3: Apilimod Synergizes with Components of CHOP

As discussed above, NHL cells demonstrated particular sensitivity to apilimod in our cancer cell line screen. DLBCL is the most common type of NHL, accounting for 30-40% of lymphomas in Western countries. DLBCL is an aggressive neoplasm of mature B cells. Approximately 40% of all DLBCL patients relapse after first line treatment. Many refractory DLBCL-GCB cancers exhibit single and double translocations of MYC and BCL2. Patients with these genetic variants tend to have a poorer prognosis due at least in part to overexpression of MYC and BCL2. Notably, apilimod was effective even in DLBCL-GCB cell lines exhibiting these translocations (Table 2), supporting a role for apilimod in the treatment of even aggressive subtypes of NHL, either alone, as monotherapy, or in combination with standard treatments.

TABLE 2

Bcl-2 and c-myc translocation status for B Cell Lymphoma Lines and their sensitivity to apilimod.

| Number | B Cell Lymphoma Model | Cell Line | IC$_{50}$ (nM) | Bcl-2 | C-myc |
|---|---|---|---|---|---|
| 7 | Human DLBCL-GCB | SUDHL-4 | 25 | Yes | Yes |
| 8 | Human DLBCL-GCB | SUDHL-6 | 80 | Yes | No |
| 9 | Human DLBCL-GCB | DB | 150 | No | No |
| 10 | Human DLBCL-GCB | Toledo | 270 | ND | ND |
| 11 | Human DLBCL-GCB | SUDHL-10 | 20 | Yes | Yes |
| 12 | Human DLBCL-GCB | WSU-DLCL2 | 160 | Yes | No |
| 13 | Human DLBCL-GCB | OCI-Ly19 | 380 | Yes | No |
| 20 | Human DLBCL-GCB | HT | 642 | ND | ND |
| 21 | Human DLBCL-GCB | Pfeiffer | 2,620 | ND | ND |

ND = No Data

To further evaluate the effectiveness of apilimod against aggressive NHL tumors, the ability of apilimod to act synergistically with any of a number of chemotherapeutic agents that comprise the standard first line treatment for many such cancers was tested. These included, for example, cyclophosphamide, doxorubicin, vincristine and prednisone (referred to as the "CHOP" chemotherapy regimen), and rituximab, which is sometimes combined with CHOP (R-CHOP), as well as the chemotherapeutic agents velcade, which is indicated for relapsed mantle cell lymphoma, and everolimus, an inhibitor of mTOR.

For synergy studies the following DLBCL-GCB cell lines were used: WSU-DLCL2, SUDHL-4 and SUDHL-6. Cells were seeded in 96 well plates at their optimum density. Cells were treated with apilimod alone (7.8-1000 nM), doxorubicin (3.13-400 nM), vincristine (0.08-10 nM), prednisone (19.5-2500 nM), velcade (0.16-20 nM), or everolimus (0.23-500 nM), either alone or in a combination with apilimod. In each case, the dilutions were 2-fold with a total of 8 dilutions over the drug concentration range.

Cells were treated for 72 h before proliferation was assessed using CellTiterGlo® (Promega). For calculation of synergy, CalcuSyn (version 2.11, Biosoft) was used to determine the combination index (CI) as defined by Chou et al., *Adv. Enzyme. Regul.* (1984) 22:27-55. Thus, drug combinations producing CI values >1 were defined as antagonistic, CI=1 as additive, and CI <1 as synergistic.

As shown in Table 3, apilimod demonstrated synergistic activity with 5 of 6 agents tested (doxorubicin, prednisolone, vincristine, velcade, and everolimus) in the SUDHL-6 cell line and was synergistic with vincristine in all three cell lines. In addition, apilimod was synergistic with prednisolone, velcade, and everolimus in at least two of the three cell lines tested. These results demonstrate that combination therapy with apilimod represents a promising new approach for addressing the unmet medical need for treatments that benefit patients who relapse after or who are refractory to standard chemotherapy regimens.

TABLE 3

| | Combination Treatment | | WSU-DLCL2 | SU-DHL-4 | SU-DHL-6 |
|---|---|---|---|---|---|
| Standard of care | Cyclophosphamide | Apilimod | ND | ND | ND |
| | Doxorubicin 50-400 nM | Apilimod 125-500 nM | Antagonistic | ND | Synergistic |
| | Prednisolone 62-1667 nM | Apilimod 62.5-500 nM | Synergistic | ND | Synergistic |
| | Vincristine 0.6-10 nM | Apilimod 62.5-1000 nM | Synergistic | Synergistic | Synergistic |
| Other therapies | Velcade 1.3-5 nM | Apilimod 62.5-250 nM | Additive | Synergistic | Synergistic |
| | Everolimus 18.5-55.6 nM | Apilimod 62.5-250 nM | Synergistic | ND | Synergistic |

Summary of drug combination effects of apilimod and individual components of CHOP (excluding cyclophosphamide), Velcade or Everolimus in DLBCL-GCB cell lines. Combination index (CI) was used to determine combination effects, where CI > 1 is antagonistic, CI = 1 is additive and CI < 1 is synergistic.
The range of concentrations of apilimod in combination with either CHOP components, Velcade or Everolimus to produce the described effect is shown (italics). \

Example 4: Synergistic Activity Between Apilimod and Ibrutinib

Studies in SUDHL-4 cells were also undertaken to screen for other drugs that could act synergistically with apilimod. A manually curated library of 93 drugs including both FDA approved and unapproved drugs was used in the screen. Cells were grown in the presence of drug, with or without apilimod (at IC$_{20}$=10 nM), with each drug of the library being tested in a 10 point-concentration response curve (1.5-30,000 nM; 3-fold dilutions). SUDHL-4 cells were grown in RPMI Medium 1640 containing (Sigma Aldrich F2442-500ML, Lot 12D370) Penicillin/Streptomycin (100×) (CellGro Ref 30-002). Cells were seeded into 96 well plates at a density of 19,000 cells per well, in a final volume of 50 µL. 50 µL of the 10 point drug dilution series (at 2×) was added to the cells to give the final concentrations stated above. Plates were incubated at 37° C. under an atmosphere of 5% CO$_2$ in a humidified incubator. 72 hours after compound addition relative cell viability was determined by CellTiter-Glo® luminescence assay (Promega) as per the manufacturer's instructions, and values were expressed as a percentage relative to vehicle (DMSO) treated control cells (set to 100%).

Figure 18:
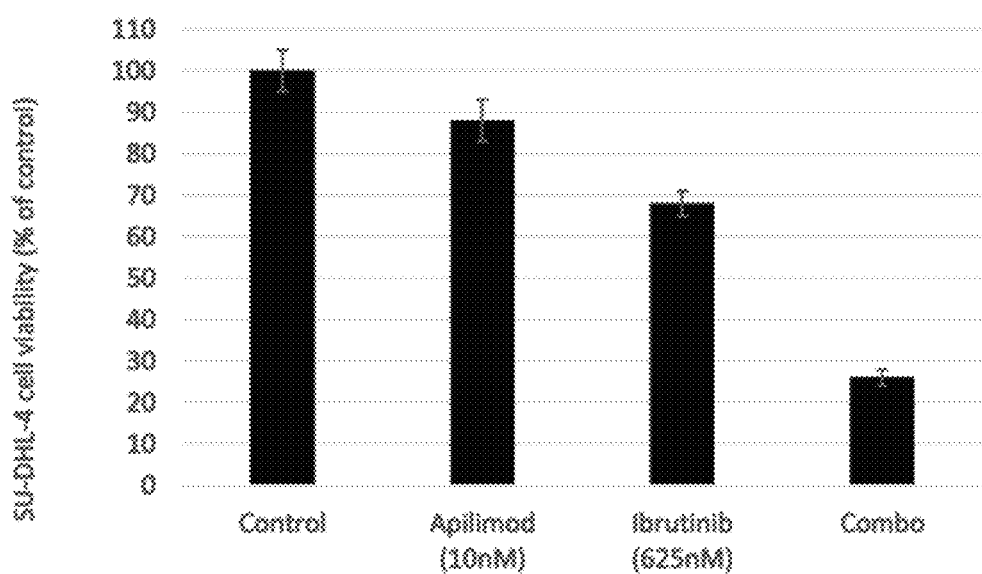
FIG. 18: Screening SU-DHL-4 cells with a manually curated library of 93 drugs with and without apilimod (10 nM) identified ibrutinib as a drug that when combined with apilimod exerts synergistic activity.
Figure 19:
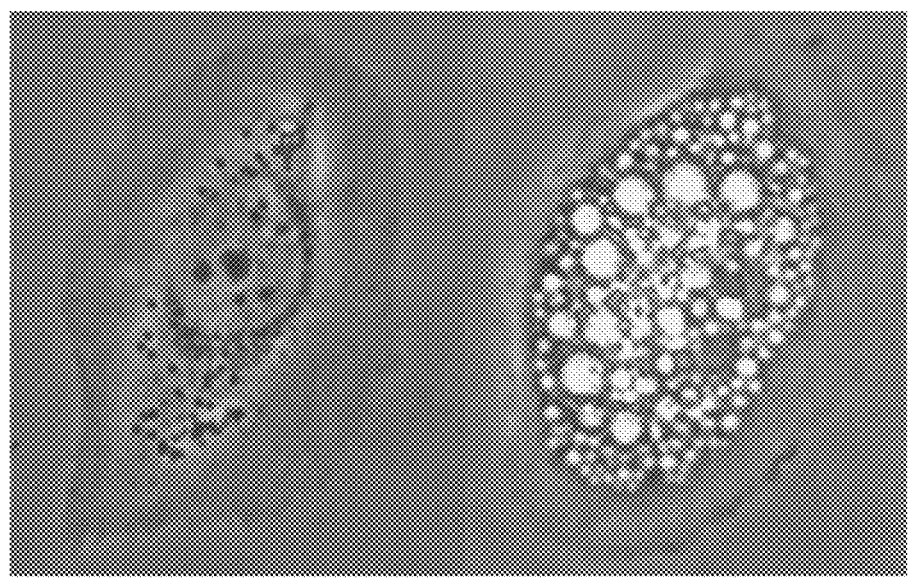
FIG. 19: Apilimod induces vacuolization of a representative cancer cell line. Left: Untreated cell. Right: Live cells treated with 500 nM apilimod 24 h.

The viability of cells treated with individual compound in the drug library was compared to the viability of cells treated with each library drug+apilimod (IC$_{20}$) and significant combinations were identified. Ibrutinib was identified as significantly reducing SUDHL-4 cell viability in the presence of apilimod compared with either ibrutinib or apilimod alone. See FIG. 18. Ibrutinib is an FDA-approved drug targeting B-cell malignancies and indicated for monotherapy in treating mantle cell lymphoma and chronic lymphocytic leukemia. It is also known as PCI-32765 and marketed under the trade name Imbruvica™. Ibrutinib is a selective and covalent inhibitor of the enzyme Bruton's tyrosine kinase (BTK). BTK is a key mediator of at least three critical B-cell pro-survival mechanisms occurring in parallel—regulation of apoptosis, cell adhesion and cell migration and homing. The synergistic activity of apilimod with ibrutinib further indicate that apilimod is a promising agent for use in combination therapy with other chemotherapy agents, especially those targeted against B-cell lymphomas.

Example 5: Anti-Tumor Activity of Apilimod in Combination with Ibrutinib on DLBCL Tumors In Vivo The ability of apilimod to inhibit tumor growth in vivo, either alone or in combination with ibrutinib was tested next. As described below, apilimod alone significantly reduced tumor growth and the combination of apilimod and ibrutinib provided greater growth inhibition than either agent alone.

The study objective was to evaluate pre-clinically the in vivo therapeutic efficacy of apilimod in the treatment of a subcutaneous SUDHL-6 human DLBCL cancer xenograft model alone, and in combination with ibrutinib.

In the first arm of the study, apilimod was tested alone. The SUDHL-6 cell line was maintained in RPMI-1640 medium supplemented with 10% fetal bovine serum and L-glutamine (2 mM) at 37° C. in an atmosphere of 5% $CO_2$. The tumor cells were sub-cultured twice weekly and harvested during exponential growth for tumor inoculation. NOD-SCID mice were γ-irradiated 24 hrs before inoculation. Each mouse was inoculated subcutaneously in the right flank with SU-DHL-6 tumor cells ($5 \times 10^6$) in 0.1 ml of PBS with Matrigel (1:1). The tumors were then grown to a mean size of approximately 80-120 mm³ and the mice were then split into 5 groups and treated as detailed in the Table 4.

TABLE 4

Xenograft Model of DLBCL tumors

| Group | Treatment | Dose | Dosing schedule | Administration route | Number of mice |
|---|---|---|---|---|---|
| 1 | Vehicle (Saline) | — | QD × 5 -2 days off- QDx5 | i.v. | 6 |
| 2 | Apilimod Dimesylate | 67.5 mg/kg (47 mg/kg Free Base) | QD × 5 -2 days off- QDx5 | i.v. | 6 |
| 3 | 0.5% Methyl-cellulose | — | BID × 5 -2 days off- BIDx5 | p.o. | 6 |
| 4 | Apilimod Free Base | 75 mg/kg | BID × 5 -2 days off- BIDx5 | p.o. | 6 |
| 5 | Apilimod Free Base | 150 mg/kg | QD × 5 -2 days off- BIDx5 | p.o. | 6 |

Figure 16:
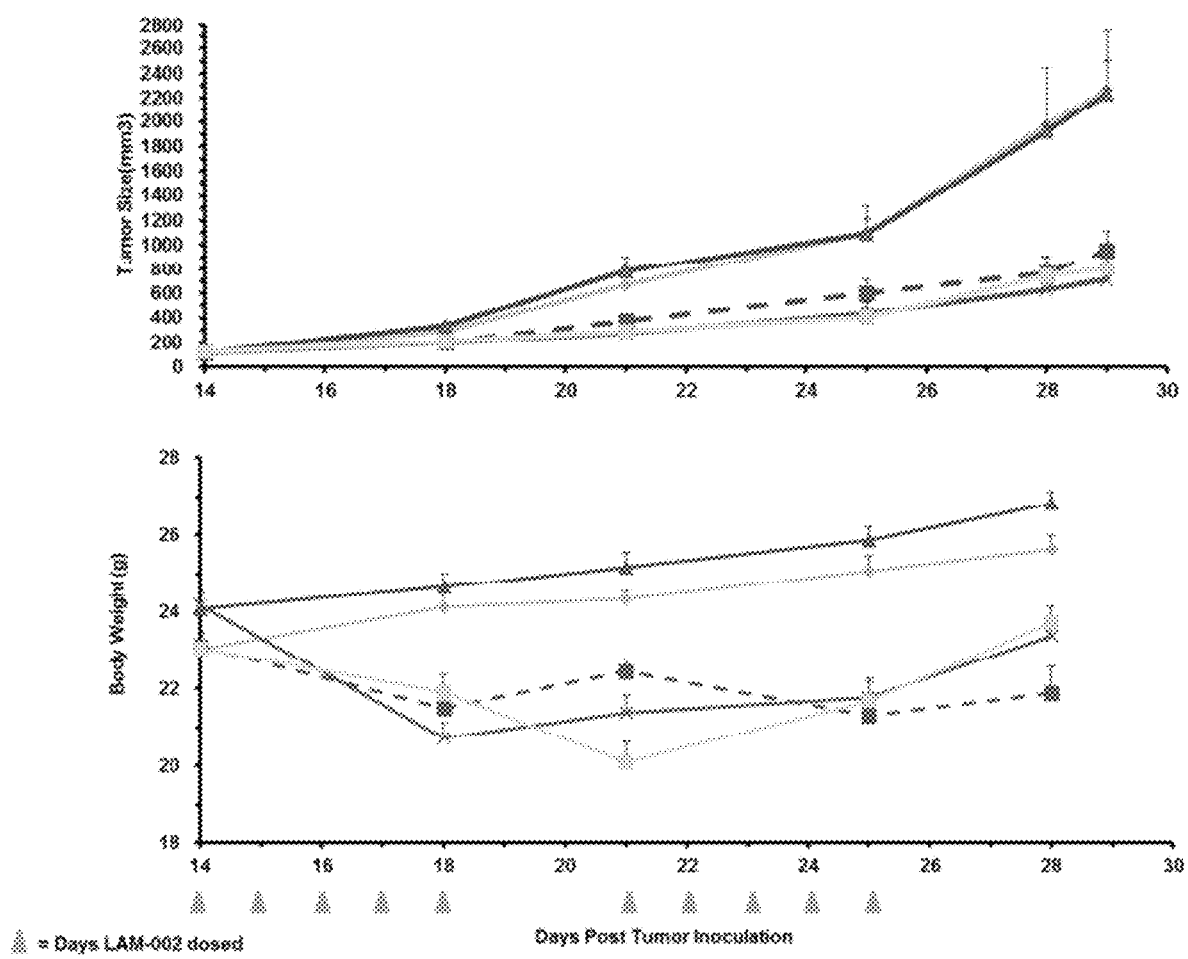
FIG. 16: Apilimod inhibits the growth of SU-DHL-6 DLBCL xenograft tumors; Top line shows vehicle saline (diamond, light grey solid lines) QD×5, 2 days off, QD×5 i.v.; 0.5% methylcellulose (triangle, solid dark grey lines) QD×5, 2 days off, QD×5 p.o.; apilimod dimesylate (square, dashed lines) 67.5 mg/kg (47 mg/kg free base) QD×5 i.v., 2 days off, QD×5; apilimod free base (square, light grey solid lines) 150 mg/kg QD×5, 2 days off, QD×5 p.o; apilimod free base (cross, solid lines) 75 mg/kg BID×5, 2 days off, BID×5 p.o.

Tumor size was measured twice a week in two dimensions using a caliper, and the volume is expressed in mm³ using the formula: $V=0.5 \, a \times b^2$ where a and b are the long and short diameters of the tumor, respectively. The mice were monitored for 29 days and significant growth inhibition was observed in all apilimod treatment arms. Intravenous administration reduced tumor size by 58% (47 mg/kg) and oral dosing reduced growth by 68% (150 mg/kg split dose) or by 64% (150 mg/kg single dose) with negligible effect on body weight (see FIG. 16). Thus, intravenous and oral administrations of apilimod displayed similar efficacy in impairing the growth of SU-DHL-6 tumors in vivo.

The second arm of the study evaluated efficacy of apilimod when combined with ibrutinib in the same SUDHL-6 human DLBCL cancer xenograft model using the same protocol as described above. Each mouse was inoculated subcutaneously in the right flank with SU-DHL-6 tumor cells ($5 \times 10^6$) in 0.1 ml of PBS with Matrigel (1:1). The tumors were then grown to a mean size of approximately 80-120 mm³ and the mice were then split into 6 groups and treated as detailed in the Table 5.

TABLE 5

SUDHL-6 cell line xenograft experiment

| Group | Treatment | Dose | Dosing schedule | Administration route | Number of mice |
|---|---|---|---|---|---|
| 1 | Vehicle | NA | QDx5-2 days off-QDx5 | p.o. + i.v. | 6 |
| 2 | Apilimod Free Base | 75 mg/kg | QDx5-2 days off-QDx5 | p.o. | 6 |
| 3 | Ibrutinib | 10 mg/kg | QD × 12 | i.v. | 6 |
| 4 | Ibrutinib | 20 mg/kg | QD × 12 | i.v. | 6 |
| 5 | Apilimod Free Base + Ibrutinib | 75 mg/kg + 10 mg/kg | QDx5-2 days off-QDx5 + QD × 12 | p.o. + i.v. | 6 |
| 6 | Apilimod Free Base + Ibrutinib | 75 mg/kg + 20 mg/kg | QDx5-2 days off-QDx5 + QD × 12 | p.o. + i.v. | 6 |

Figure 17:
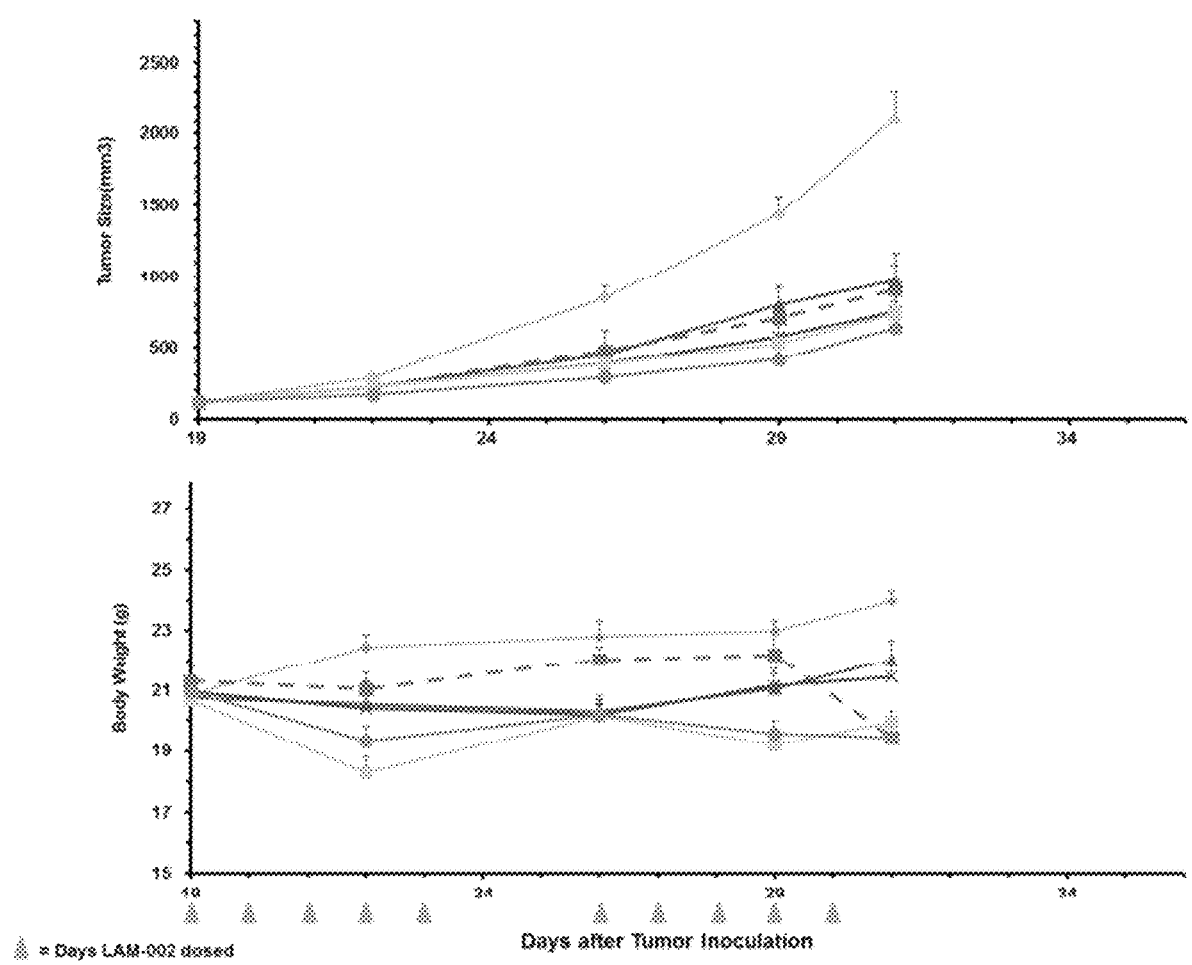
FIG. 17: Antitumor activity of apilimod in combination with ibrutinib on DLBCL tumors in vivo; Top line shows vehicle (diamond, light grey solid lines) QD×5, 2 days off, QD×5 p.o.+i.v.; ibrutinib (triangle, solid dark grey lines) 10 mg/kg QD×12 i.v.; apilimod free base (square, dashed lines) 75 mg/kg QD×5, 2 days off, QD×5 p.o.; ibrutinib (cross, solid dark line) 20 mg/kg QD×12 i.v.; apilimod free base 75 mg/kg QD×5, 2 days off, QD×5 p.o.+ibrutinib 10 mg/kg QD×12 i.v. (square, solid light grey lines); apilimod free base 75 mg/kg QD×5, 2 days off, QD×5 p.o.+ibrutinib 10 mg/kg QD×12 i.v. (circle, solid medium grey lines).

Tumor size was measured twice a week in two dimensions using a caliper, and the volume is expressed in mm³ using the formula: $V=0.5 \, a \times b^2$ where a and b are the long and short diameters of the tumor, respectively. The mice were monitored for 31 days and significant growth inhibition was observed in the 75 mg/kg apilimod (57%), 10 mg/kg ibrutinib (54%), and 20 mg/kg ibrutinib (64%) treatment arms. The combination of 75 mg/kg apilimod with ibrutinib further reduced tumor growth in a dose dependent manner; 10 mg/kg ibrutinib (65%) and 20 mg/kg ibrutinib (70%) (see FIG. 17).

Example 6: Apilimod is a Highly Selective Binder of PIKfyve Kinase

In order to identify the cellular target of apilimod in cancer cells, whole cell lysate prepared from human neuroglioma cells was used to identify its binding partners using chemical capture mass spectrometry (CCMS). This work was performed at Caprotec Bioanalytics GmbH, Berlin Germany. See Michaelis et al., *J. Med. Chem.*, 55 3934-44 (2012) and references cited therein. Briefly, two capture compound variants employing apilimod as selectivity function attached in a single orientation were synthesized and analyzed by LC-MS and 1H-NMR to ensure identity and purity. Capture conditions were optimized in whole cell lysate, e.g. minimization of non-specific interactions of the proteins with capture compounds, concentration of reagents and proteins to obtain maximum binding of proteins and capture compounds, etc. One capture compound was selected to identify specific protein binders in the CCMS experiments using apilimod as a competitor ligand. Proteins that are detected by LC-S in the capture assay and that are significantly diminished in competition control experiments are considered to be specific binders. These specific binders were further subjected to stringent data analysis criteria to determine specificity after unbiased data evaluation. Specific protein binders were ranked according to their fold change (FC) values in the capture experiments. Only two proteins were identified as high probability candidate target proteins of apilimod: PIKfyve and Vac14. FC and p-values for these proteins in the four different capture compound concentration experiments are shown in Table 6.

TABLE 6

| | | Capture Compound Concentrations | | | |
|---|---|---|---|---|---|
| | | 0.1 µM | 0.5 µM | 1.0 µM | 2.0 µM |
| PIKfyve | log$_2$ (FC) | 6.3 | 6.2 | 4.1 | 4.3 |
| | −log$_{10}$ (p-value) | 3.7 | 2.8 | 5.1 | 3.9 |
| Vac14 | log$_2$ (FC) | 6.2 | 5.6 | Inf. | 3.9 |
| | −log$_{10}$ (p-value) | 3.9 | 3.8 | 1.9 | 3.6 |

Figure 7:
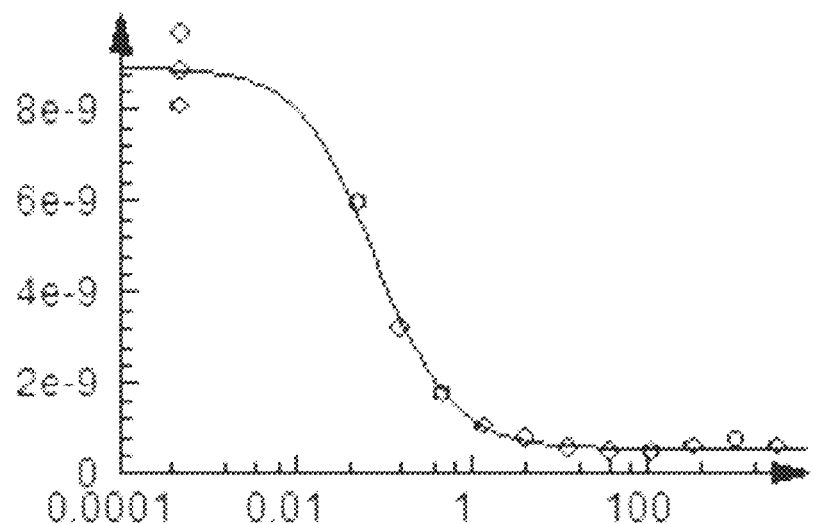
FIG. 7: Apilimod binds with high affinity to PIKfyve (Kd=75 pM).
Figure 8:
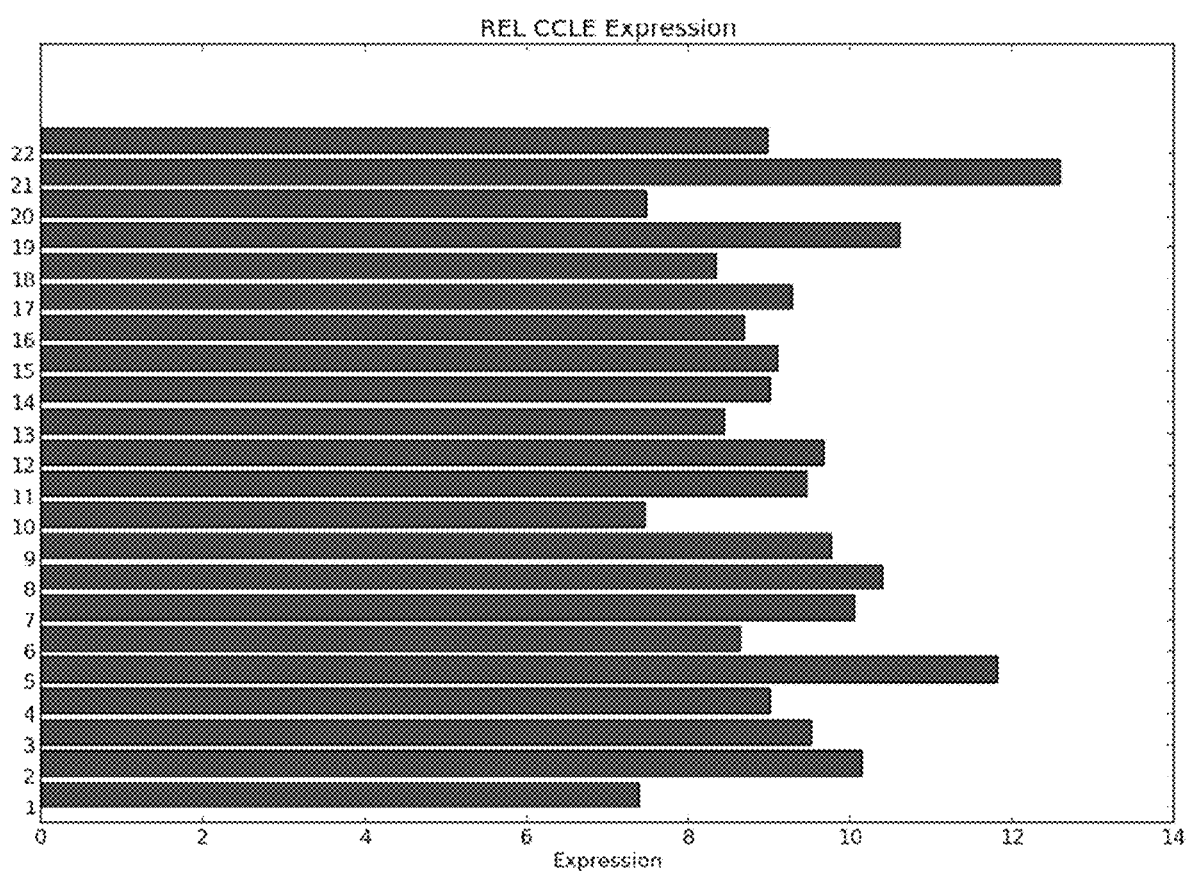
FIG. 8: REL CCLE expression in apilimod sensitive (lines #1-13) and insensitive (lines #14-22) B cell lymphoma lines.
Figure 9:
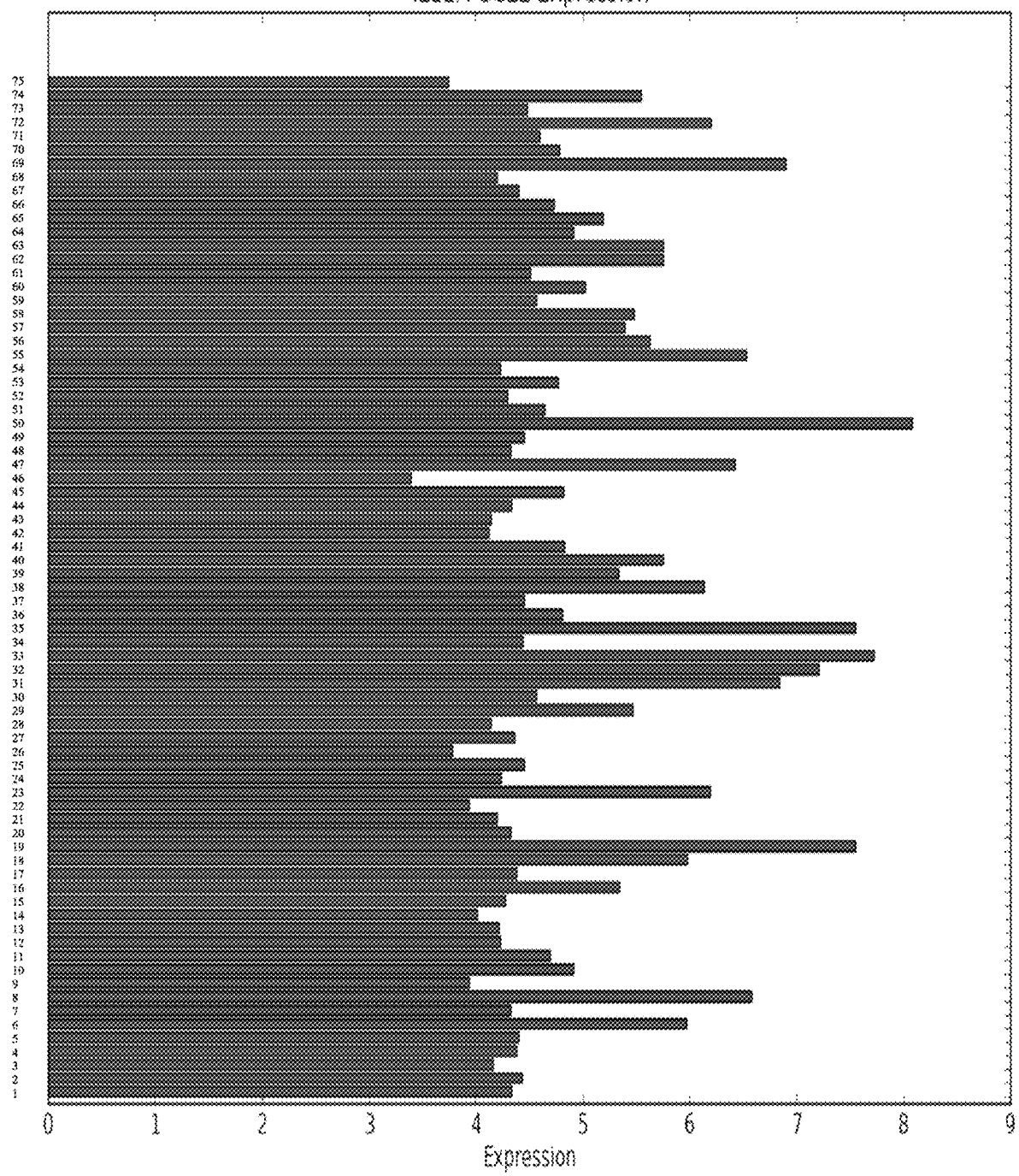
FIG. 9: IL12A CCLE expression in apilimod sensitive (#1-23 lines) and insensitive (#24-75 lines) cancer cell lines.
Figure 10:
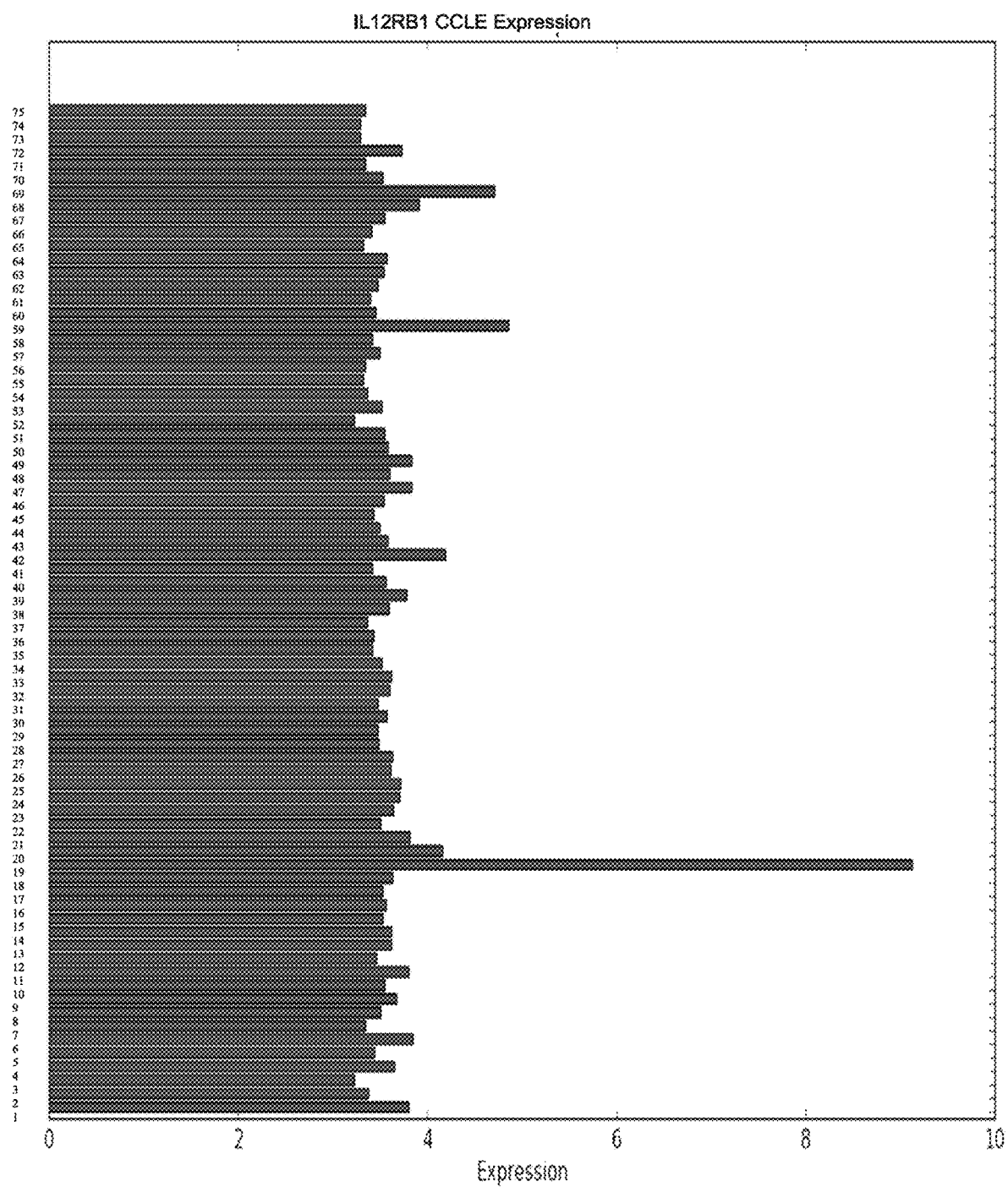
FIG. 10: IL12B CCLE expression in apilimod sensitive (#1-23 lines) and insensitive (#24-75 lines) cancer cell lines.
Figure 11:
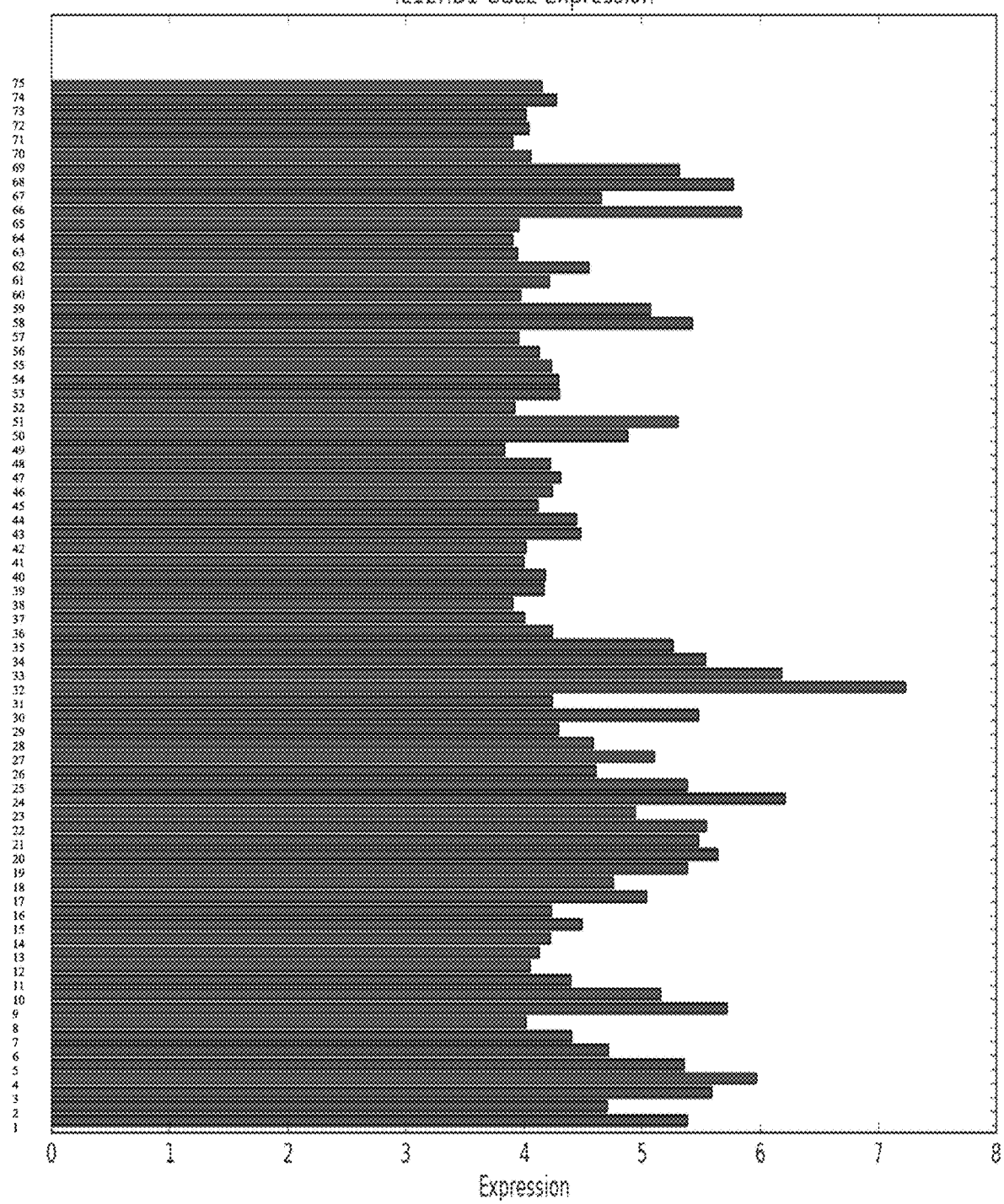
FIG. 11: IL12RB1 CCLE expression in apilimod sensitive (#1-23 lines) and insensitive (#24-75 lines) cancer cell lines
Figure 12:
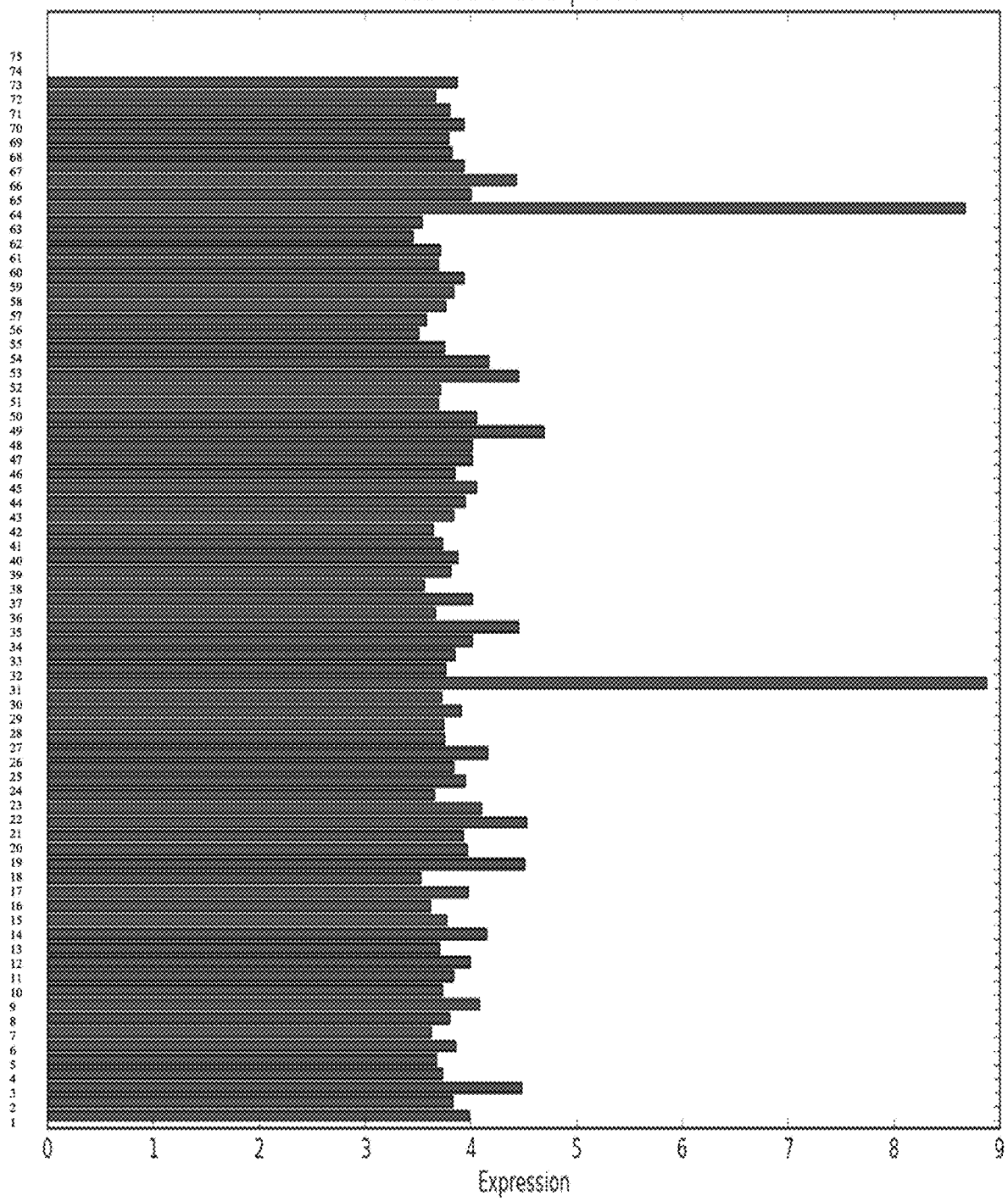
FIG. 12: IL12RB2 CCLE expression in apilimod sensitive (#1-23 lines) and insensitive (#24-75 lines) cancer cell lines.
Figure 13:
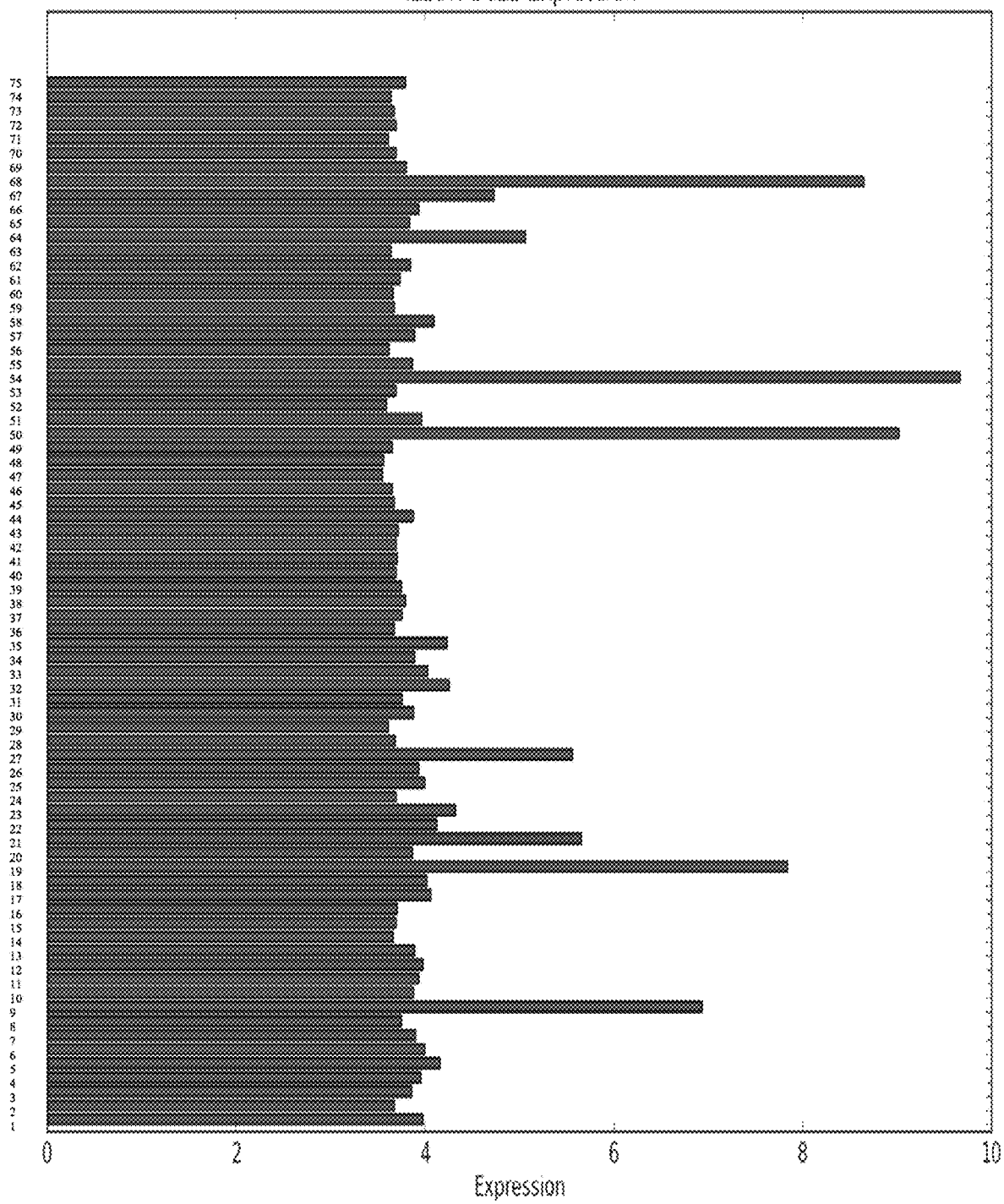
FIG. 13: IL23R CCLE expression in apilimod sensitive (#1-23 lines) and insensitive (#24-75 lines) cancer cell lines.
Figure 14:
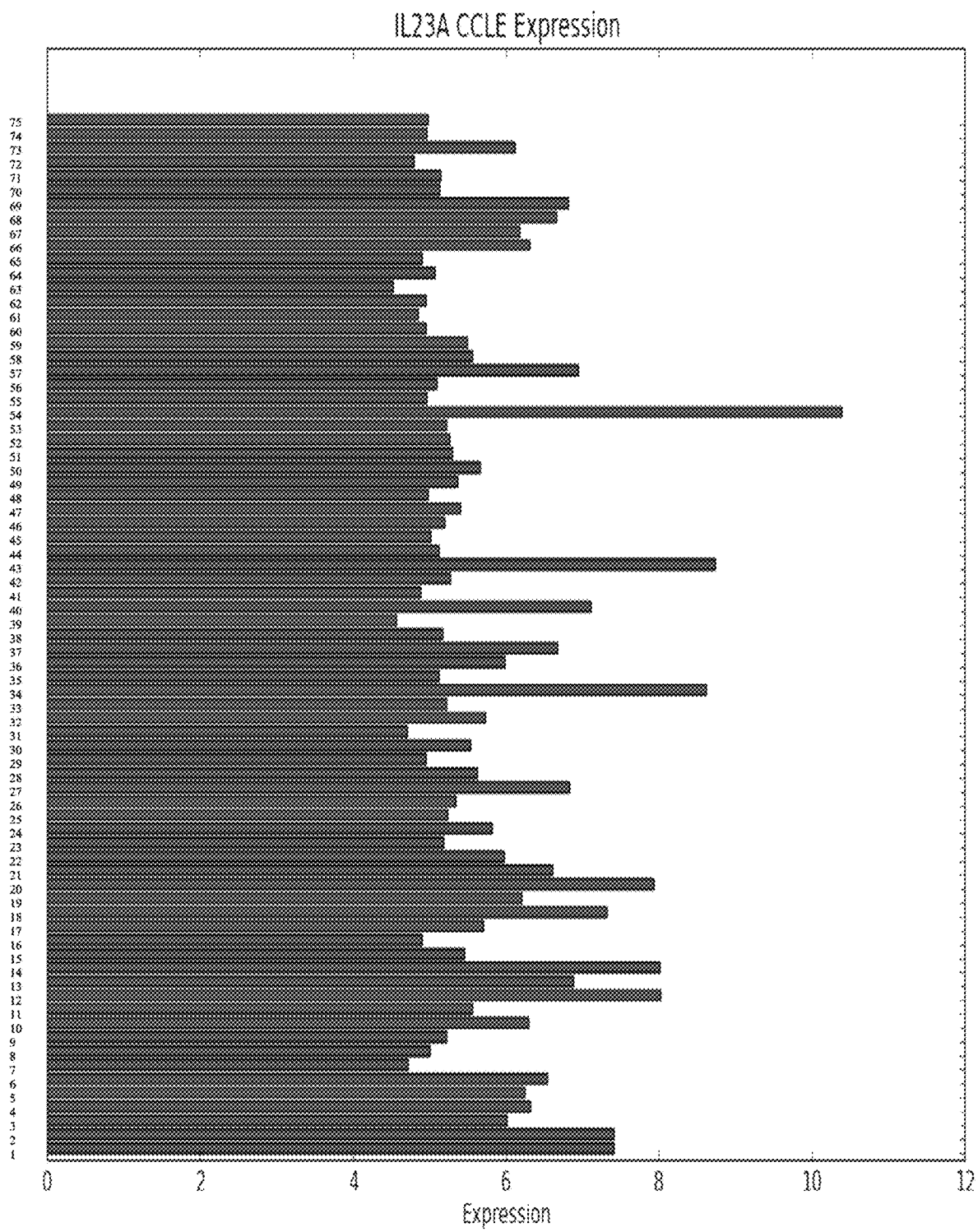
FIG. 14: IL23A CCLE expression in apilimod sensitive (#1-23 lines) and insensitive (#24-75 lines) cancer cell lines.

In a separate study, protein kinase profiling of apilimod was conducted to identify kinase targets (DiscoveRx, Fremont, Calif.). A dissociation constant ($K_d$) study was performed using apilimod at increasing concentrations (0.05-3000 nM) against PIKfyve, a known target of apilimod. The experiment was performed in duplicate and the $K_d$ was determined to be 0.075 nM (range 0.069-0.081 nM) (FIG. 7).

Next, apilimod was screened against a comprehensive panel of kinases (PIKfyve not included). In total, 456 kinases, including disease-relevant kinases, were assayed for their ability to bind with apilimod. The screening concentration of apilimod was 1 µM, a concentration that is >10,000 times greater than the $K_d$ for apilimod against PIKfyve. The results from the screen showed that apilimod did not bind to any of the 456 kinases tested.

Together, these results demonstrate that apilimod binds with high selectivity in cancer cells to a single cellular kinase, PIKfyve. PIKfyve is an enzyme that binds to PI(3)P and catalyzes the formation of the lipid second messengers PI(3,5)P2 and PI(5)P and others have shown that apilimod is also a potent and specific inhibitor of this kinase PIKfyve in normal cells. Cai X et al., Chem Biol. 2013 Jul. 25; 20(7): 912-21. As discussed in more detail below, in order to understand the mechanism of apilimod's selective cytotoxicity against cancer cells, we conducted a series of experiments aimed at elucidating its biological activity in cancer cells.

Example 7: Mechanism of Anti-Cancer Activity of Apilimod

Apilimod is known to be a potent inhibitor of the inflammatory cytokines IL-12 and IL-23. To the extent apilimod was indicated for treating a disease or disorder, it was predicated on this activity. Although the clinical testing of apilimod focused on its potential efficacy in autoimmune and inflammatory diseases such as psoriasis, rheumatoid arthritis, and Crohn's disease, there were a few published suggestions that apilimod might be useful against cancers, and specifically against cancers in which c-rel or IL-12/23 were acting as pro-proliferative factors. See e.g., WO 2006/128129 and Baird et al., Frontiers in Oncology 3:1 (2013), respectively. Surprisingly, and contrary to these expectations predicated on apilimod's IL-12/23 inhibitory activity, we found no correlation between any of c-Rel expression (c-Rel is a transcription factor for the IL-12/23 genes), IL-12, or IL-23 expression and sensitivity to apilimod in the tested cell lines (see FIGS. 8-14).

Briefly, gene expression data from the Cancer Cell Line Encyclopedia (CCLE) was analyzed for the 22 B cell lymphoma lines for which we obtained dose response curves against apilimod (see Table 7).

TABLE 7

22 B Cell Lymphoma Lines analyzed for gene expression and response to apilimod. Epstein Barr status and nuclear cREL status is noted.

| Number | B Cell Lymphoma Model | Cell Line | IC50 (nM) | EBV | Nuclear REL |
|---|---|---|---|---|---|
| 1 | Human Burkitt's lymphoma | ST486 | 25 | No | ND |
| 2 | Human Burkitt's lymphoma | Daudi | 200 | Yes | Yes |
| 3 | Human Burkitt's lymphoma | EB1 | 174 | Yes | ND |
| 4 | Human Burkitt's lymphoma | GA-10 | 382 | No | ND |
| 5 | Human Mantle Cell Lymphoma | Rec-1 | 300 | No | ND |
| 6 | Human Mantle Cell Lymphoma | JeKo-1 | 70 | No | ND |
| 7 | Human Diffuse Large B Cell Lymphoma -GCB | SUDHL-4 | 25 | No | Yes |
| 8 | Human Diffuse Large B Cell Lymphoma -GCB | SUDHL-6 | 80 | No | ND |
| 9 | Human Diffuse Large B Cell Lymphoma -GCB | DB | 150 | No | ND |
| 10 | Human Diffuse Large B Cell Lymphoma -GCB | Toledo | 270 | No | ND |
| 11 | Human Diffuse Large B Cell Lymphoma -GCB | SUDHL-10 | 20 | No | ND |
| 12 | Human Diffuse Large B Cell Lymphoma -GCB | WSU-DLCL2 | 160 | No | ND |
| 13 | Human Diffuse Large B Cell Lymphoma -GCB | OCI-Ly19 | 380 | Yes | ND |
| 14 | Human Burkitt's lymphoma | Namalwa | 600 | Yes | ND |
| 15 | Human Burkitt's lymphoma | CA46 | >10,000 | No | ND |
| 16 | Human Burkitt's lymphoma | Raji | >10,000 | Yes | Yes |
| 17 | Human Mantle Cell Lymphoma | GRANTA-519 | >10,000 | Yes | ND |
| 18 | Human Follicular B Cell Lymphoma | RL | >10,000 | ND | ND |
| 19 | Human Follicular Lymphoma - DLBCL-GCB | DOHH-2 | 700 | No | ND |
| 20 | Human Diffuse Large B Cell Lymphoma -GCB | HT | 642 | No | ND |
| 21 | Human Diffuse Large B Cell Lymphoma -GCB | Pfeiffer | 2,620 | ND | ND |
| 22 | Human Diffuse Large B Cell Lymphoma -GCB | KARPAS-422 | >10,000 | No | ND |

ND = No Data

Expression of c-REL was compared in sensitive (IC$_{50}$ less than 500 nM) and insensitive (IC$_{50}$ greater than 500 nM) lines by unpaired t-test. No statistically significant relationship between c-REL expression and sensitivity was found (p=0.97). Furthermore, no detection of a significant relationship between sensitivity to apilimod and either the presence of constitutive nuclear c-REL or infection with Epstein Barr virus in cell lines for which data has been published was found. The cell lines tested included the following apilimod sensitive (#1-13) and insensitive (#14-22) B cell lymphoma lines: Human Burkitt's lymphoma cell lines 1-4 (ST486, Daudi, EB1, GA-10), Human Mantle Cell Lymphoma 5-6 (Rec-1, JeKo-1), Human Diffuse Large B Cell Lymphoma-GCB 7-13 (SUDHL-4, SUDHL-6, DB, Toledo, SUDHL-10, WSU-DLCL2, OCl-Ly19), Human Burkitt's Lymphoma 14-16 (Namalwa, CA46, Raji), Human Mantle Cell Lymphoma 17 (GRANTA-519), Human Follicular B Cell Lymphoma 18 (RL), Human Follicular Lymphoma-DLBCL-GCB 19 (DOHH-2), Human Diffuse Large B Cell Lymphoma-GCB (HT, Pfeiffer, KARPAS-422).

The expression of IL-12A, IL-12RB1, IL-12RB2, IL-12B, IL-23A and IL-23R was further analyzed in a diverse group of 75 cancer cell lines, including the aforementioned 22 lymphoma lines (see Table 8).

TABLE 8

Various Cancer cell lines

| Number | Cancer Model | Cell Line | IC50 (nM) |
|---|---|---|---|
| 1 | Human Burkitt's lymphoma | ST486 | 25 |
| 2 | Human Mantle Cell Lymphoma | JeKo-1 | 70 |
| 3 | Human Diffuse Large B Cell Lymphoma -GCB | SUDHL-4 | 25 |
| 4 | Human Diffuse Large B Cell Lymphoma -GCB | SUDHL-6 | 80 |
| 5 | Human Burkitt's lymphoma | Daudi | 200 |
| 6 | Human histiocytic lymphoma | U937 | 106 |
| 7 | Human lung carcinoma | A549 | 110 |
| 8 | Human colorectal cancer | HCT116 | 125 |
| 9 | Human B-cell lymphoma | DB | 150 |
| 10 | Human Diffuse Large B Cell Lymphoma -GCB | WSU-DLCL2 | 160 |
| 11 | Human Colorectal | HCT-15 | 200 |
| 12 | Human Colorectal | SW480 | 90 |
| 13 | Human Colorectal | COLO-205 | 380 |
| 14 | Human Colorectal | SW620 | 90 |
| 15 | Human T-cell leukemia | Jurkat | 200 |
| 16 | Human neuroglioma | H4 | 250 |
| 17 | Human Diffuse Large B Cell Lymphoma -GCB | Toledo | 270 |
| 18 | Human B cell Non-Hodgkin's Lymphoma | Rec-1 | 300 |
| 19 | Human Hodgkin's lymphoma | KMH-2 | 181 |
| 20 | Human Burkitt's lymphoma | EB1 | 174 |
| 21 | Human Diffuse Large B Cell Lymphoma -GCB | SUDHL-10 | 20 |
| 22 | Human Burkitt's lymphoma | GA-10 | 382 |
| 23 | Human Diffuse Large B Cell Lymphoma -GCB | OCI-Ly19 | 380 |
| 24 | Human Diffuse Large B Cell Lymphoma -GCB | HT | 642 |
| 25 | Human Diffuse Large B Cell Lymphoma -GCB | Pfeiffer | 2,620 |
| 26 | Human Burkitt's lymphoma | Namalwa | 600 |
| 27 | Human Follicular B Cell Lymphoma-GCB | DOHH-2 | 700 |
| 28 | Human Bladder carcinoma (GATOR-/-) | SW780 | 1000 |
| 29 | Human colorectal cancer | MDST8 | 1000 |
| 30 | Human Burkitt's lymphoma | Raji | 10,000 |
| 31 | Human Hodgkin's lymphoma | HD-MyZ | >1000 |
| 32 | Human Hodgkin's lymphoma | L540 | >1000 |
| 33 | Human Hodgkin's lymphoma | HDLM-2 | >1000 |
| 34 | Human Burkitt's lymphoma | CA46 | >10,000 |
| 35 | Human Anaplastic Large Cell Lymphoma | SUDHL-1 | 590 |
| 36 | Human lung carcinoma | H1734 | 1500 |
| 37 | Human colorectal cancer | SW1116 | 1500 |
| 38 | Human Colorectal | COLO-320DM | 2,060 |
| 39 | Human neuroblastoma | A172 | 2000 |
| 40 | Human lung carcinoma | H1693 | 2000 |
| 41 | Human lung carcinoma | H460 | >2000 |
| 42 | Human lung carcinoma | H358 | >2000 |
| 43 | Human pancreatic cancer | CAPAN2 | >2000 |
| 44 | Human pancreatic cancer | PANC1 | >2000 |
| 45 | Human pancreatic cancer | MiaPaCa-2 | >2000 |
| 46 | Human pancreatic cancer | AsPC1 | >2000 |
| 47 | Human prostate cancer | DU145 | >2000 |
| 48 | Human acute myelogenous leukemia | KG-1 | >2500 |
| 49 | Human prostate cancer | LnCap | 3000 |
| 50 | Human T-cell lymphoma | HH | 3,300 |
| 51 | Human T-cell leukemia | MOLT-4 | 3,300 |
| 52 | Human prostate cancer | 22RV1 | >5000 |
| 53 | Human colorectal cancer | DLD-1 | >5000 |
| 54 | Human myelogenous leukemia | K562 | >5000 |
| 55 | Human colorectal cancer | RKO | >5000 |
| 56 | Human ovarian | TOV-21G | 7000 |
| 57 | Human prostate cancer | PC-3 | 10,000 |
| 58 | Human Hodgkin's lymphoma | L428 | 10,000 |
| 59 | Human plasmacytoma | RPMI-8226 | >10,000 |
| 60 | Human lung carcinoma | NCI-1975 | >10,000 |
| 61 | Human breast cancer | CAMA1 | >10,000 |
| 62 | Human neuroblastoma | SW1088 | >10,000 |
| 63 | Human neuroblastoma | M0591K | >10,000 |
| 64 | Human neuroblastoma | U-118 MG | >10,000 |
| 65 | Human neuroblastoma | U-87 MG | >10,000 |
| 66 | Human acute monocytic leukemia | THP1 | >10,000 |
| 67 | Human Diffuse Large B Cell Lymphoma -GCB | KARPAS-422 | >10,000 |
| 68 | Human Follicular B Cell Lymphoma | RL | >10,000 |
| 69 | Human Mantle Cell Lymphoma | GRANTA-519 | >10,000 |
| 70 | Human bronchioalveolar | NCI-H1650 | >20,000 |
| 71 | Human bronchioalveolar | SW1573 | >20,000 |
| 72 | Human bronchioalveolar | NCI-H1781 | >20,000 |
| 73 | Human bronchioalveolar | NCI-H1666 | 20,000 |
| 74 | Human Colorectal | LOVO | >10,000 |
| 75 | Human Colorectal | HT-29 | >10,000 |

Figure 15:
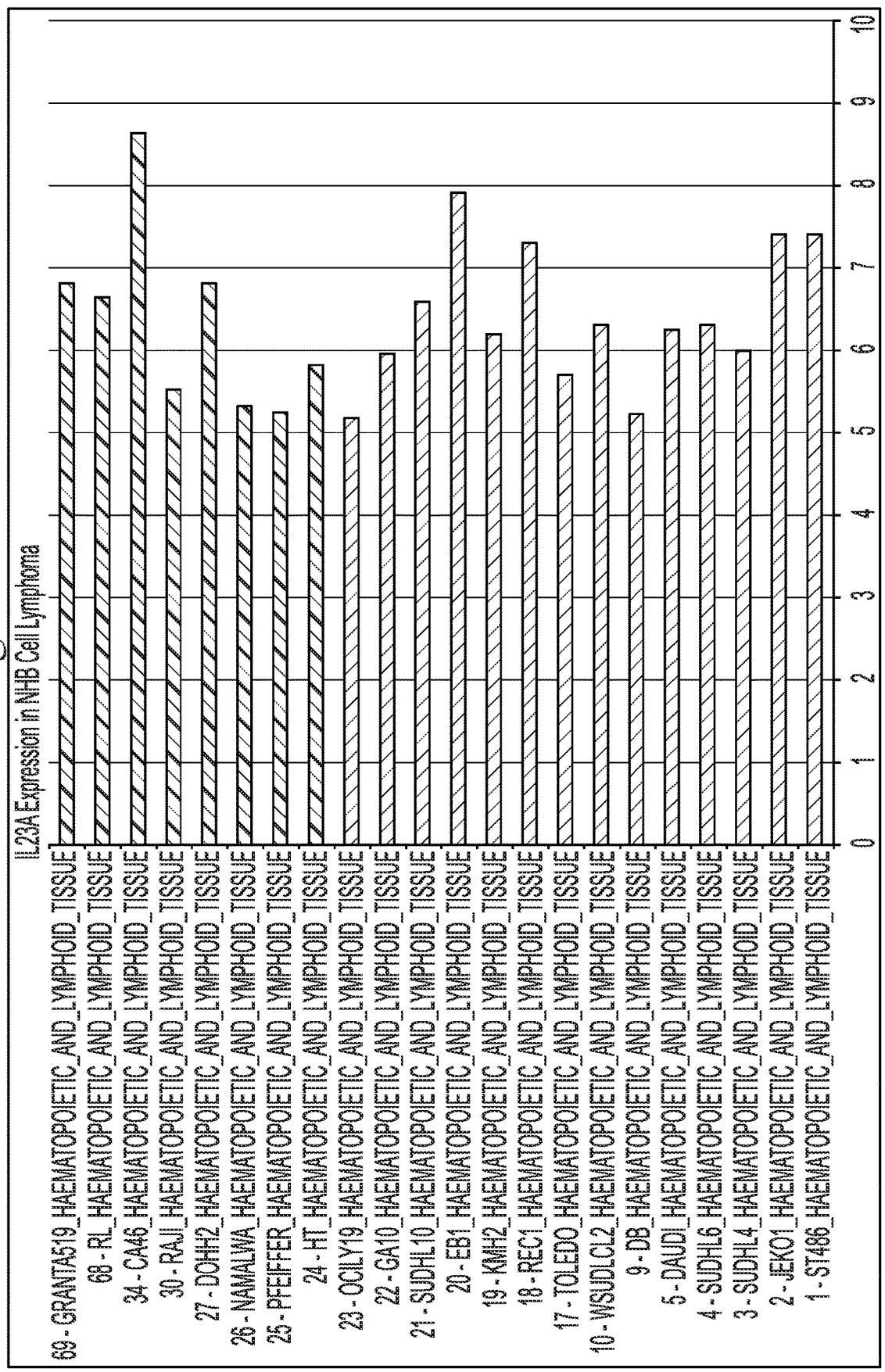
FIG. 15: IL-23A expression is not a statistically significant predictor of sensitivity in Non-Hodgkin's B cell lymphoma. Shown are apilimod sensitive NHB cell lines (bottom, dark) and insensitive (top, light).

Briefly, gene expression data from the CCLE was analyzed for the 75 cancer cell lines for which dose response curves against apilimod were obtained. The expression of each interleukin gene was compared in sensitive ($IC_{50}$ less than 500 nM) and insensitive ($IC_{50}$ greater than 500 nM) lines by unpaired t-test. No statistically significant relationship was found with the sole exception of IL-23A (p=0.022). IL-23A has been previously noted to be elevated in apilimod sensitive non small cell lung cancer lines, and recombinant IL-23A was noted to increase proliferation of non small cell lung cancer lines (see Baird et al. 2013, supra). Importantly, the statistical significance of IL-23A expression in sensitive cancer lines appears to be driven entirely by just two colon cancer lines. Furthermore IL-23A expression is not a statistically significant predictor of sensitivity in Non-Hodgkin's B cell lymphoma (FIG. 15). Global gene expression data from the CCLE database was analyzed for a reliable two gene biomarker for apilimod sensitivity in the 22 B cell lymphoma lines.

Figure 4:
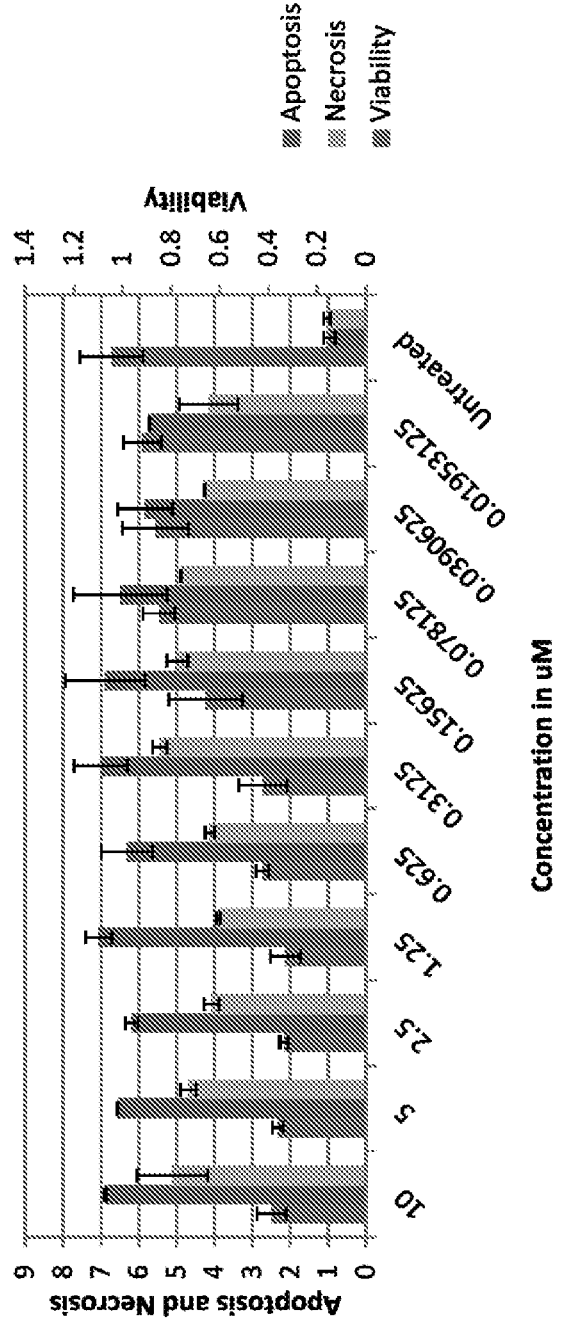
FIG. 4: Apilimod's cytotoxic activity in NHL cells was a result of increased apoptosis. Apoptotic (Caspase-3/7, middle bar) and necrotic (bis-AAF-R110, right bar) markers in apilimod treated diffuse large B cell lymphoma cells 48 hours after addition of apilimod to the culture media; left bar shows viability marker (GF-AFC).

Additional experiments demonstrated that apilimod's cytotoxic activity was based at least in part on its inducing cellular apoptosis. Apoptosis was quantified and distinguished from necrosis using the Apotox-Glo Triplex assay (Promega, Inc.) according to the manufacturer's instructions. In this assay, viability, apoptosis, and necrosis are assessed simultaneously using three different markers (GF-AFC, Caspase-3/7, and bis-AAF-R110, respectively). FIG. 4 shows apoptotic (middle bar) and necrotic (right bar) markers in apilimod treated in diffuse large B cell lymphoma cells 48 hours after addition of apilimod to the culture media. The left bar shows the viability marker.

Figure 5:
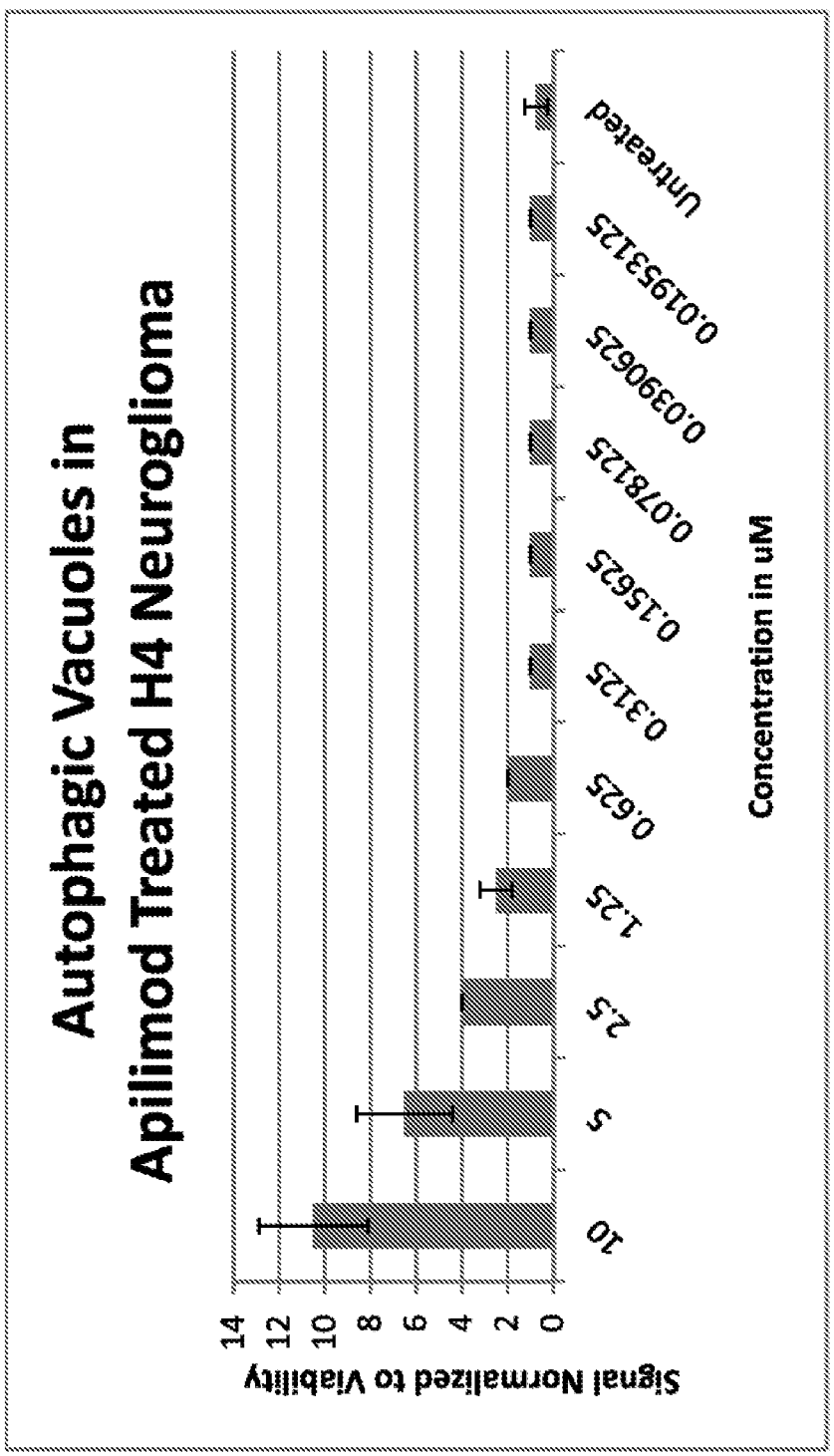
FIG. 5: Apilimod induces autophagy in a dose-dependent manner.
Figure 6:
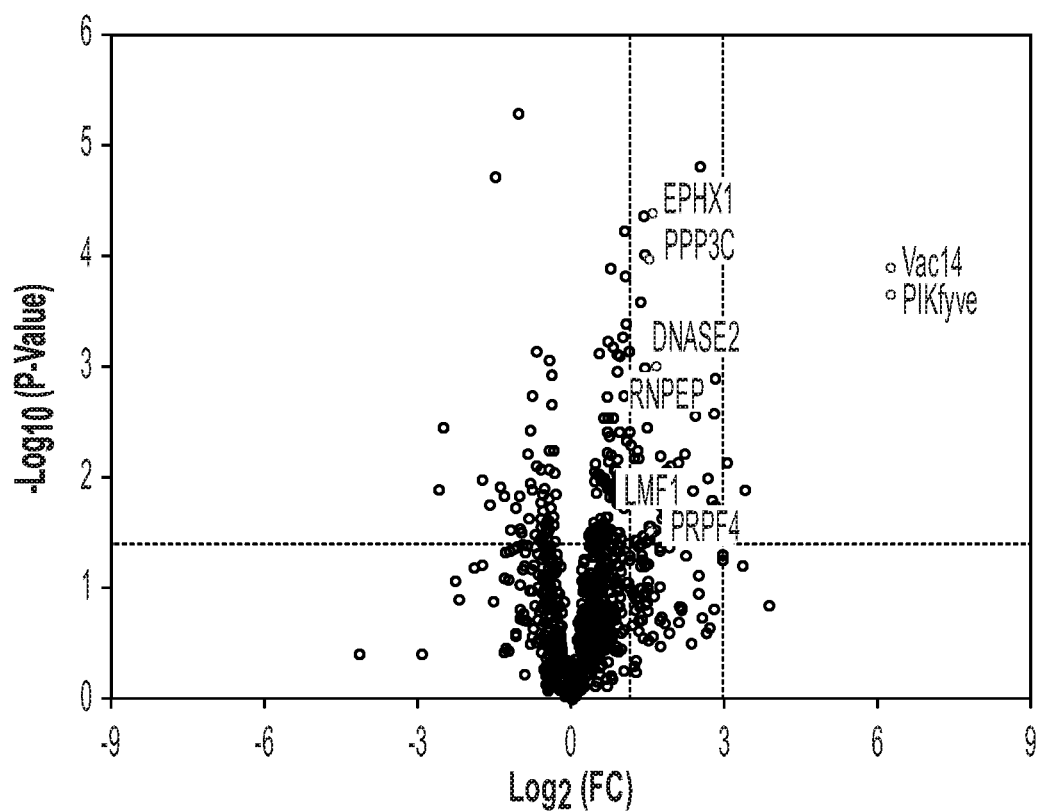
FIG. 6: Volanco plot of significant captured hits applying CT-689 at 0.1 μM concentration under optimized capture conditions.

The mechanism of apilimod's cytotoxic activity was further investigated by assaying for autophagic vacuoles after 72 hours of treatment in an H4 neuroglioma cell line ($IC_{50}$ 250-300 nM). Autophagy was quantified using the Cyto-ID Autophagy detection kit (Enzo) according to manufacturer's directions. FIG. 5 shows that apilimod induced autophagy in a dose-dependent manner.

PIKfyve is associated with the cytosolic leaflet of early endosomes and its activity is required for endomembrane homeostasis, endolysosomal function and proper retrograde transport from the endosome to the trans-Golgi network. Introduction of a kinase dead mutant into cells induces a swollen vacuole phenotype that can be rescued by the injection of PI(3,5)P2. Inhibition of PIKfyve by pharmacological methods as well as RNAi also produces swollen vacuoles and disruption of endomembrane dynamics. As shown in FIG. 21, pharmacological disruption of PIKfyve with apilimod induces selective lethality of specific cancer cell lines through disruption of intracellular trafficking.

What is claimed is:

1. A method for treating a follicular lymphoma in a human subject in need thereof, the method comprising administering a pharmaceutical composition comprising apilimod, or a pharmaceutically acceptable salt thereof, to the subject in a therapeutically effective amount.

2. The method of claim 1, wherein the pharmaceutical composition is an oral dosage form.

3. The method of claim 1, wherein the pharmaceutically acceptable salt is selected from a sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, besylate, gentisinate, fumarate, gluconate, glucaronate, saccharate, formate, benzoate, glutamate, ethanesulfonate, benzenesulfonate, p-toluenesulfonate, and pamoate.

4. The method of claim 3, wherein the pharmaceutically acceptable salt is selected from a chloride, mesylate, fumarate, lactate, maleate, pamoate, phosphate, and tartrate.

5. The method of claim 1, wherein the method comprises administering the apilimod, or pharmaceutically acceptable salt thereof, in combination with at least one additional active agent.

6. The method of claim 5, wherein the at least one additional active agent is administered in the same dosage form as the apilimod, or in a separate dosage form.

7. The method of claim 5, wherein the at least one additional active agent is rituximab.

8. The method of claim 1, wherein the human subject in need is one whose follicular lymphoma is refractory or recurrent.

9. The method of claim 7, wherein the human subject in need is one whose follicular lymphoma is refractory or recurrent.

* * * * *